(12) United States Patent
Yokota et al.

(10) Patent No.: US 11,951,422 B2
(45) Date of Patent: Apr. 9, 2024

(54) FILTRATION FILTER

(71) Applicant: Murata Manufacturing Co., Ltd., Nagaokakyo (JP)

(72) Inventors: Shusuke Yokota, Nagaokakyo (JP); Takashi Kondo, Nagaokakyo (JP); Masaru Banju, Nagaokakyo (JP); Miwako Nishikawa, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 658 days.

(21) Appl. No.: 17/108,340

(22) Filed: Dec. 1, 2020

(65) Prior Publication Data
US 2021/0077925 A1    Mar. 18, 2021

Related U.S. Application Data

(63) Continuation of application No. PCT/JP2019/031197, filed on Aug. 7, 2019.

(30) Foreign Application Priority Data

Aug. 23, 2018   (JP) .................................. 2018-155942

(51) Int. Cl.
*B01D 29/31* (2006.01)
*B01D 39/20* (2006.01)
(Continued)

(52) U.S. Cl.
CPC ......... *B01D 29/31* (2013.01); *B01D 39/2027* (2013.01); *C12M 33/14* (2013.01);
(Continued)

(58) Field of Classification Search
CPC ................ B01D 29/31; B01D 39/2027; B01D 2201/4038; B01D 2201/184; C12M 33/14; C12M 37/02
(Continued)

(56) References Cited

U.S. PATENT DOCUMENTS

2017/0212022 A1   7/2017   Kawara et al.
2019/0017012 A1   1/2019   Banju et al.

FOREIGN PATENT DOCUMENTS

JP    S4895341 A    12/1973
JP    H09276636 A   10/1997
(Continued)

OTHER PUBLICATIONS

International Search Report Issued for PCT/JP2019/031197, dated Oct. 29, 2019.
(Continued)

*Primary Examiner* — Claire A Norris
(74) *Attorney, Agent, or Firm* — Arentfox Shiff LLP

(57) ABSTRACT

A filtration filter having a tubular shape, defining a first opening and a second opening facing the first opening, and including a filter base that defines a plurality of through holes arranged in a square grid array. The filter base includes a continuous portion having a first set of through holes of the plurality of through holes, and a non-continuous portion having a second set of through holes of the plurality of through holes. The continuous portion extends in a first direction from the first opening of the filtration filter toward the second opening and extends in a second direction along at least a first portion of a circumference of the filtration filter orthogonal to the first direction. The non-continuous portion has the second set of through holes shifted relative to the first set of through holes of the continuous portion and extends in the first direction.

20 Claims, 17 Drawing Sheets

(51) Int. Cl.
    *C12M 1/12*    (2006.01)
    *C12M 1/26*    (2006.01)
(52) U.S. Cl.
    CPC ....... *C12M 37/02* (2013.01); *B01D 2201/184* (2013.01); *B01D 2201/4038* (2013.01)
(58) Field of Classification Search
    USPC .................................................. 210/497.01
    See application file for complete search history.

(56) References Cited

FOREIGN PATENT DOCUMENTS

| | | | |
|---|---|---|---|
| JP | 3196305 U | 3/2015 | |
| JP | 2017169551 A | 9/2017 | |
| JP | 2017213564 A | 12/2017 | |
| KR | 20150060194 A | * | 6/2015 |

OTHER PUBLICATIONS

Written Opinion of the International Searching Authority issued for PCT/JP2019/031197, dated Oct. 29, 2019.

* cited by examiner

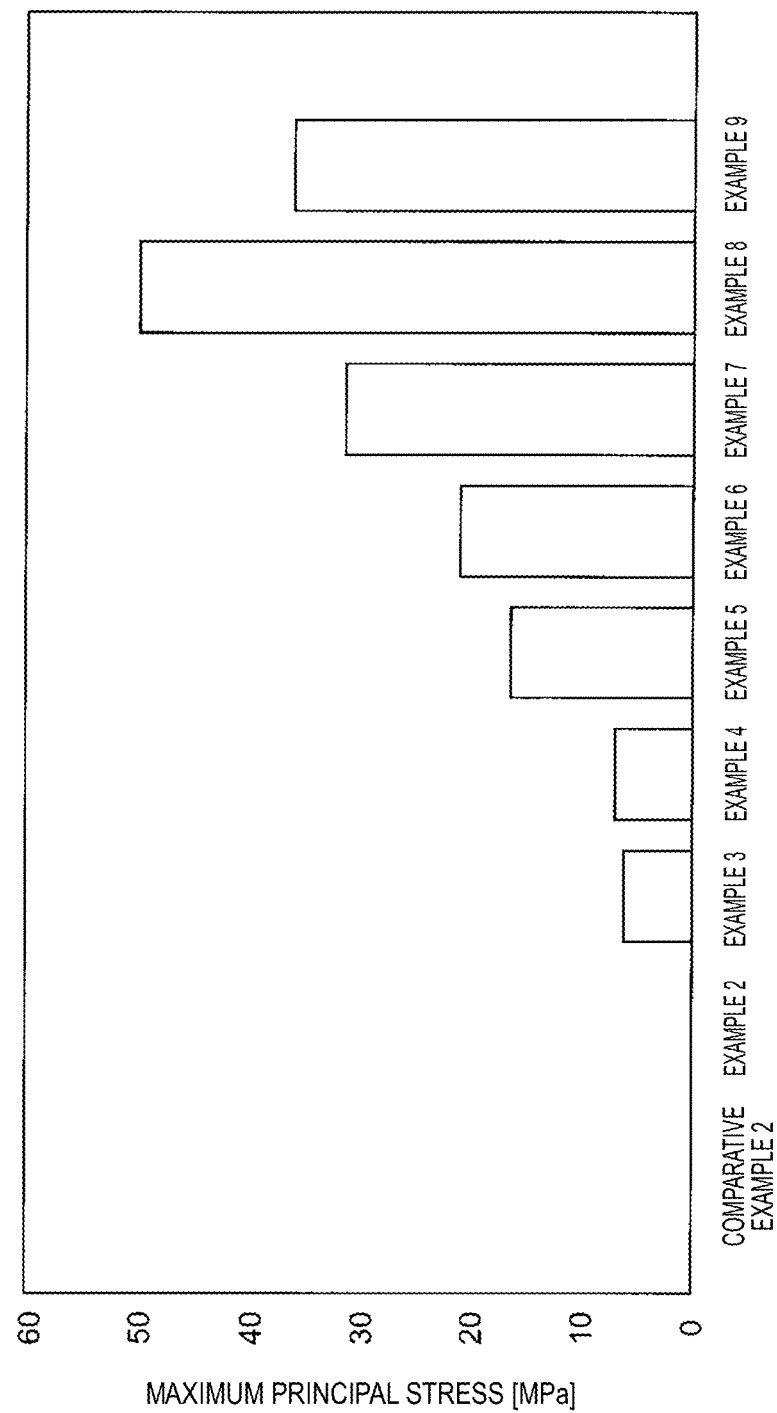

FILTRATION FILTER

CROSS REFERENCE TO RELATED APPLICATIONS

The present application is a continuation of International application No. PCT/JP2019/031197, filed Aug. 7, 2019, which claims priority to Japanese Patent Application No. 2018-155942, filed Aug. 23, 2018, the entire contents of each of which are incorporated herein by reference.

FIELD OF THE INVENTION

The present invention relates to a filtration filter.

BACKGROUND OF THE INVENTION

Examples of known filters include a filter having a cylindrical shape (for example, see Patent Document 1).

The filter in Patent Document 1 includes an inner tubular wire mesh, a filter body, and an outer tubular wire mesh. Overlapping portions of the inner tubular wire mesh in the longitudinal direction are welded together. To form the filter body, a felt sheet made of metal fiber is wound around the inner tubular wire mesh such that the wound felt sheet has a predetermined thickness, and the filter body is impregnated with a heat-resistant resin and then dried. Overlapping portions of the outer tubular wire mesh in the longitudinal direction are welded together.

Patent Document 1: Japanese Unexamined Patent Application Publication No. 9-276636

SUMMARY OF THE INVENTION

In recent years, filtration filters that have a tubular shape and that can be easily cut by an external force have been in demand.

An object of the present invention is to provide a filtration filter that can be easily cut by an external force.

A filtration filter of an aspect of the present invention has a tubular shape and defines a first opening and a second opening facing the first opening. The filtration filter includes a filter base that defines a plurality of through holes arranged in a square grid array. The filter base includes a continuous portion having a first set of through holes of the plurality of through holes, and a non-continuous portion having a second set of through holes of the plurality of through holes. The continuous portion extends in a first direction from the first opening of the filtration filter toward the second opening of the filtration filter and extends in a second direction along at least a first portion of a circumference of the filtration filter orthogonal to the first direction. The non-continuous portion has the second set of through holes shifted relative to the first set of through holes of the continuous portion and extends in the first direction.

According to the present invention, it is possible to provide a filtration filter that can be easily cut by being subjected to an external force.

BRIEF DESCRIPTION OF THE DRAWINGS

FIG. 14 illustrates the relationships between the maximum principal stresses in Example 2 to Example 9 relative to the maximum principal stress in Comparative Example 2.

DETAILED DESCRIPTION OF THE PREFERRED EMBODIMENTS

Figure 1:
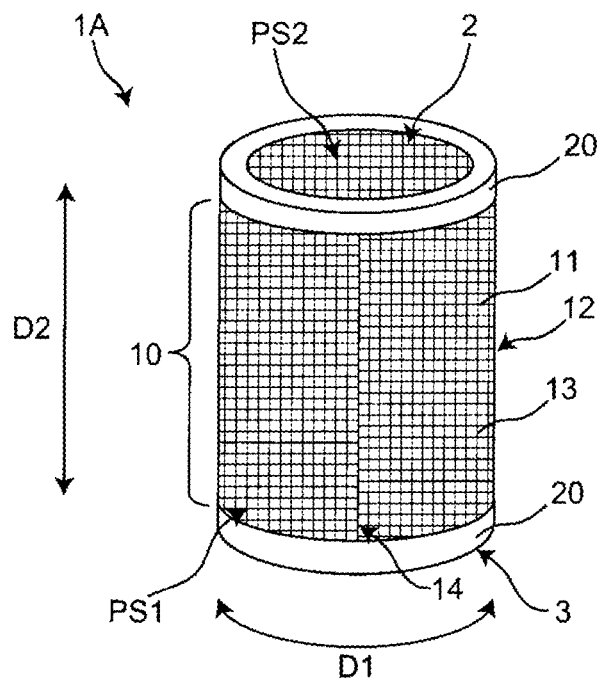
FIG. 1 is a schematic perspective view of an example of a filtration filter in Embodiment 1 according to the present invention.

In recent years, there has been an increasing demand for observing the filtration objects captured by a tubular filtration filter after a fluid containing the filtration objects is filtered by cross-flow filtration. For example, there is a demand for observing filtration objects by performing filtration with a filtration filter and by setting, on an optical microscope, the filtration filter that has captured the filtration objects.

However, such a tubular filtration filter captures filtration objects inside the filtration filter, and thus it is difficult to observe the filtration objects captured by the filtration filter. For this reason, after filtration is performed, the filtration objects captured inside the filtration filter are observed by applying an external force to the filtration filter to cut the filtration filter.

A tubular filtration filter that is not broken by being subjected to the force of a fluid during filtration and that can be easily cut by an external force after the filtration is finished is in demand under such circumstances.

The present inventors have completed the following invention to provide a tubular filter that can be easily cut by an external force while maintaining sufficient strength to withstand filtration.

A filtration filter of an aspect of the present invention has a tubular shape and defines a first opening and a second opening facing the first opening. The filtration filter includes a filter base that defines a plurality of through holes arranged in a square grid array. The filter base includes a continuous portion having a first set of through holes of the plurality of through holes, and a non-continuous portion having a second set of through holes of the plurality of through holes. The continuous portion extends in a first direction from the first opening of the filtration filter toward the second opening of the filtration filter and extends in a second direction along at least a first portion of a circumference of the filtration filter orthogonal to the first direction. The non-continuous portion has the second set of through holes shifted relative to the first set of through holes of the continuous portion and extends in the first direction.

Such a configuration enables the filtration filter having a tubular shape to be easily cut by being subjected to an external force.

The filter base includes a first filter base extending in the first direction in the non-continuous portion, the first filer base having a first side and a second side opposite the first side; a plurality of second filter bases connected to the first side of the first filter base at respective first connection portions, the plurality of second filter bases extending in the second direction; and a plurality of third filter bases connected to the second side of the first filter base at respective second connection portions, the plurality of third filter bases extending in the second direction. The respective plurality of first connection portions and the respective plurality of second connection portions may be shifted relative to each other in the first direction.

With such a configuration, connection points are formed at respective positions in the first filter base forming the non-continuous portion where the first filter base and the second filter bases extending in the circumferential direction of the filtration filter are connected and where the first filter base and the third filter bases extending in the circumferential direction of the filtration filter are connected. As a result, stress is likely to be generated in the non-continuous portion. Thus, the filtration filter can be more easily cut.

The respective first connection portions may be each disposed between a corresponding adjacent two of the respective second connection portions.

Such a configuration enables the filtration filter having a tubular shape to be more easily cut by being subjected to an external force.

The width of the first filter base may be equal to the width of a part of the continuous portion of the filter base.

Such a configuration enables the filtration filter having a tubular shape to be even more easily cut by being subjected to an external force.

The filtration filter is a film filter having a first end joined to a second end to form the tubular shape. The non-continuous portion may be in a joint region where the first end and the second end are joined.

Such a configuration enables the non-continuous portion to be easily formed and the filtration filter having a tubular shape to be even more easily cut by being subjected to an external force.

The filter base may contain at least one of a metal and a metal oxide as a main component thereof.

With such a configuration, the filtration filter having a tubular shape can be easily cut by being subjected to an external force while having improved mechanical strength.

Embodiment 1 according to the present invention is described below with reference to the accompanying drawings. The drawings illustrate emphasized components to facilitate descriptions.

Embodiment 1

[Overall Configuration]

Figure 2:
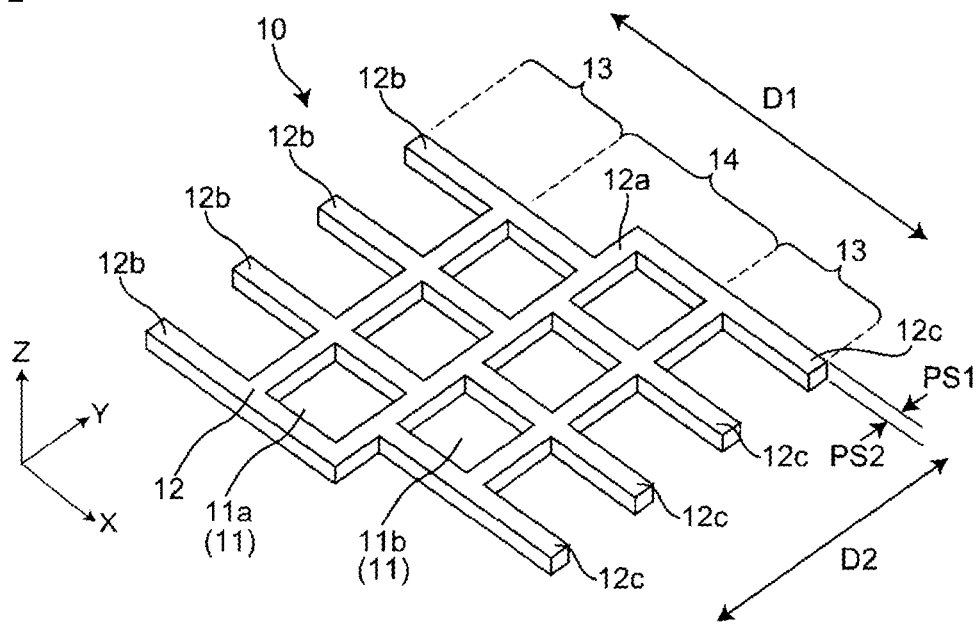
FIG. 2 is an enlarged schematic perspective view of a part of a non-continuous portion of a filter portion in FIG. 1.
Figure 3:
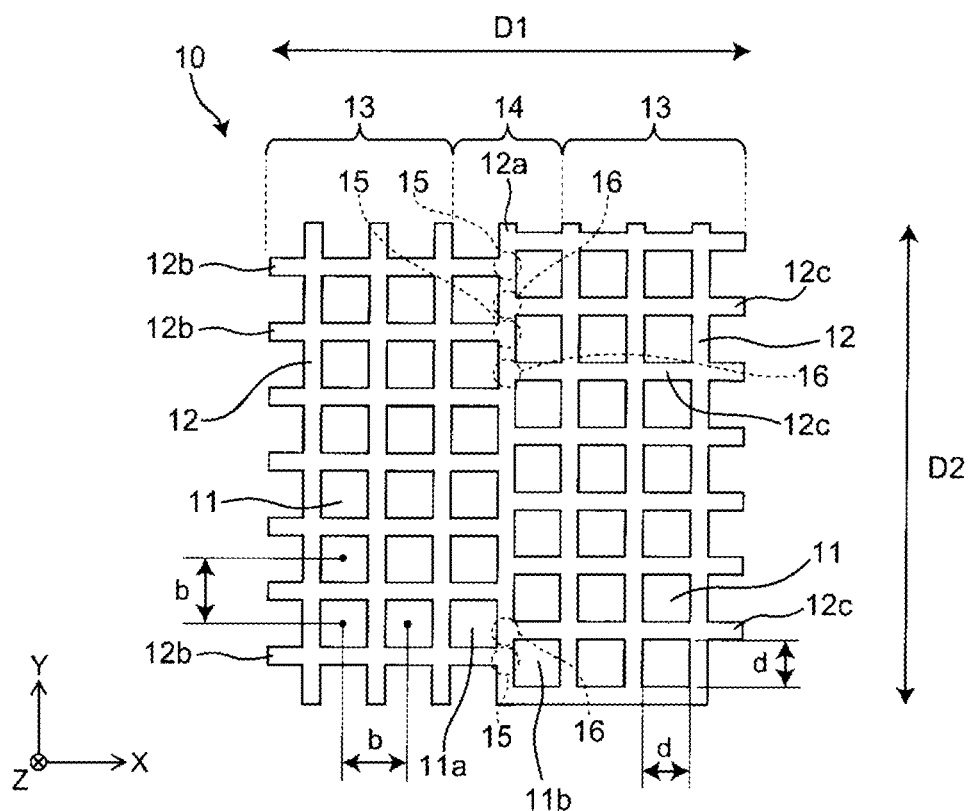
FIG. 3 is an enlarged schematic plan view of a part of the non-continuous portion of the filter portion in FIG. 1.

FIG. 1 is a schematic perspective view of an example of a filtration filter 1A in Embodiment 1 according to the present invention. FIG. 2 is an enlarged schematic perspective view of a part of a non-continuous portion 14 of a filter portion 10 in FIG. 1. FIG. 3 is an enlarged schematic plan view of a part of the non-continuous portion 14 of the filter portion 10 in FIG. 1. A direction D1 in FIG. 1 is the circumferential direction of the filtration filter 1A. A direction D2 in FIG. 1 is a direction orthogonal to the circumferential direction of the filtration filter 1A. The X direction in FIGS. 2 and 3 is the lateral direction of the filtration filter 1A. The Y direction in FIGS. 2 and 3 is the longitudinal direction of the filtration filter 1A. The Z direction in FIGS. 2 and 3 is the thickness direction of the filtration filter 1A.

As illustrated in FIG. 1, the filtration filter 1A is shaped into a cylinder having a first opening 2 and a second opening 3 facing the first opening 2. The first opening 2 and the second opening 3 face each other in the longitudinal direction (Y direction) of the filtration filter 1A. In the description, the circumferential direction D1 denotes the direction that is orthogonal to the direction D2 from the first opening 2 of the filtration filter 1A toward the second opening 3 of the filtration filter 1A and that circles along the shape of a circumferential portion of the filtration filter 1A. Specifically, the circumferential direction D1 denotes the direction along the circumference of a section of the filtration filter 1A in the direction orthogonal to the direction D2 from the first opening 2 of the filtration filter 1A toward the second opening 3 of the filtration filter 1A. In Embodiment 1, the circumferential direction D1 denotes the circumferential direction of the filtration filter 1A.

In Embodiment 1, the filtration filter 1A includes the filter portion 10 and frame portions 20. The filter portion 10 is shaped into a hollow cylinder. The frame portions 20 are disposed at the respective ends of the filter portion 10 and are each shaped into a ring.

Although an example in which the filtration filter 1A includes the frame portions 20 is described in Embodiment 1, the frame portions 20 are not essential components. In addition, although the filtration filter 1A having a cylindrical shape is described as an example in Embodiment 1, the shape of the filtration filter 1A is not limited to a cylindrical shape. It is simply required that the filtration filter 1A have a tubular shape.

In Embodiment 1, the filtration filter 1A is shaped into a cylinder by rolling a rectangular film filter having a first main surface PS1 and a second main surface PS2 facing the first main surface PS1. The first main surface PS1 is positioned at the outer surface of the filtration filter 1A having a cylindrical shape. The second main surface PS2 is positioned at the inner surface of the filtration filter 1A having a cylindrical shape.

The filtration filter 1A is a filter usable for cross-flow filtration. A fluid containing filtration objects flows inside the cylinder of the filtration filter 1A. As a result, the filtration objects are captured by the second main surface PS2 of the filtration filter 1A, and some of the fluid flows from the second main surface PS2 of the filtration filter 1A toward the first main surface PS1 of the filtration filter 1A.

In the description, the term "filtration objects" denotes objects that are contained in a fluid and that are to be filtered. For example, filtration objects may be powders or minute particles. In addition, filtration objects may be biological substances contained in a fluid. The term "biological substances" denotes substances derived from living things such as cells (eukaryotes), bacteria (eubacteria), and viruses. Examples of cells (eukaryotes) include induced pluripotent stem (iPS) cells, ES cells, stem cells, mesenchymal stem cells, mononuclear cells, single cells, cell masses, floating cells, adherent cells, nerve cells, white blood cells, cells for regenerative medicine, autologous cells, cancer cells, circulating tumor cells (CTC), HL-60, HELA, and fungi. Examples of bacteria (eubacteria) include colon bacilli and tubercle bacilli.

As illustrated in FIGS. 1 to 3, the filter portion 10 is formed by a filter base 12, which defines a plurality of through holes 11. The through holes 11 are arranged periodically. In Embodiment 1, the through holes 11 are arranged in a square grid array. The filter base 12, which forms the filter portion 10, contains at least one of a metal and a metal oxide as a main component. The filter base 12 may be made of, for example, gold, silver, copper, platinum, nickel, palladium, titanium, an alloy thereof, or an oxide thereof.

The filter base 12 includes a continuous portion 13, which is formed continuously into a grid-like pattern, and the non-continuous portion 14, which is formed by shifting the continuous portion 13 in the direction D2 orthogonal to the circumferential direction D1 of the filtration filter 1A.

As illustrated in FIGS. 2 and 3, the continuous portion 13 is formed continuously into a grid-like pattern. The expression "formed continuously into a grid-like pattern" denotes that the parts of the filter base 12 extending in the circumferential direction D1 (X direction) of the filtration filter 1A are formed so as not to have an inflection point and that the parts of the filter base 12 extending in the longitudinal direction (Y direction) of the filtration filter 1A are formed so as not to have an inflection point. In Embodiment 1, the filter base 12 is integrally formed.

In other words, the expression "formed continuously into a grid-like pattern" denotes that the parts of the filter base 12 extending in the longitudinal direction (Y direction) of the filtration filter 1A are formed continuously in the direction D2 from the first opening 2 of the filtration filter 1A toward the second opening 3 of the filtration filter 1A and that the parts of the filter base 12 extending in the circumferential direction D1 (X direction) of the filtration filter 1A are formed continuously in the circumferential direction D1 along the circumference of a section of the filtration filter 1A in the direction orthogonal to the direction D2 from the first opening 2 of the filtration filter 1A toward the second opening 3 of the filtration filter 1A.

In the continuous portion 13, the through holes 11 are arranged periodically such that the Hamiltonian has translational symmetry. For example, the continuous portion 13 denotes that the parts of the filter base 12 extending in the circumferential direction D1 of the filtration filter 1A or the parts of the filter base 12 extending in the direction D2 orthogonal to the circumferential direction D1 have local periodicity. In Embodiment 1, the direction D2 orthogonal to the circumferential direction D1 denotes the direction from the first opening 2 toward the second opening 3.

As described above, in the filter base 12, the continuous portion 13 is formed continuously into a grid-like pattern. Thus, the through holes 11 defined by the filter base 12 are periodically arranged in the first main surface PS1 and the second main surface PS2 of the filter portion 10. Specifically, the through holes 11 are disposed in the filter portion 10 in a matrix at regular intervals.

In Embodiment 1, the through holes 11 each have a square shape when viewed from the first main surface PS1 of the filter portion 10, that is, in the Z direction. The through holes 11 are disposed at regular intervals in two array directions parallel to the sides of each square when viewed from the first main surface PS1 of the filter portion 10 (in the Z direction). That is, the through holes 11 are disposed at regular intervals in the X direction and the Y direction in FIGS. 2 and 3. As described above, the open area percentage can be increased by disposing the through holes 11 in a square grid array, and thus it is possible to reduce the resistance generated by a fluid passing through the filtration filter 1A.

The intervals between the through holes 11 are appropriately determined according to the type (size, shape, property, or elasticity) or the amount of filtration objects. As illustrated in FIG. 3, the interval between the through holes 11 denotes an interval b between the center of one of the through holes 11 and the center of a through hole 11 adjacent to the one of the through holes 11 when the through holes 11 are viewed from the first main surface PS1 of the filter portion 10. In the case of a periodically arranged structure, the interval b between the through holes 11 is, for example, more than one times and ten times or less the length of a side d of the through hole 11, preferably three times or less the length of the side d of the through hole 11. The open area percentage of the filter portion 10 is, for example, 10% or more, preferably 25% or more. Such a configuration enables the resistance generated by a fluid passing through the filter portion 10 to be reduced. The open area percentage is calculated by dividing the area of the through holes 11 by the projected area of the first main surface PS1 under the assumption that the through holes 11 are not open.

The thickness of the filter portion 10 is preferably one-tenth to ten times the size (side d) of the through hole 11, more preferably more than half to ten times the size (side d) of the through hole 11. Such a configuration enables the resistance of the filtration filter 1A against a fluid to be reduced. As a result, it is possible to reduce the stress on filtration objects.

In the filter portion 10, preferably, the second main surface PS2, with which a fluid containing filtration objects comes into contact, has low surface roughness. The surface roughness denotes the average of the difference between the maximum value and the minimum value of surface roughness that are measured with a stylus profilometer at five randomly selected positions on the second main surface PS2. In Embodiment 1, preferably, the surface roughness is less than the size of a filtration object, more preferably less than half the size of a filtration object. In other words, the through holes 11 in the second main surface PS2 of the filter portion 10 are formed on the same plane (XY-plane). The filter base 12, which is the part of the filter portion 10 in which the through holes 11 are not formed, is continuous and integrally formed. Such a configuration enables the adhesion of filtration objects to the second main surface PS2 of the filter portion 10 to be reduced and thus the resistance of a fluid to be reduced.

In each of the through holes 11, the opening closer to the first main surface PS1 and the opening closer to the second main surface PS2 are in communication with each other via continuous wall surfaces. Specifically, in each of the through holes 11, the opening closer to the first main surface PS1 is disposed so as to be able to be projected on the opening closer to the second main surface PS2. That is, the through holes 11 are each disposed such that the opening closer to the first main surface PS1 and the opening closer to the second main surface PS2 overlap each other when the filter portion 10 is viewed from the first main surface PS1.

The shape (sectional shape) of the through hole 11 projected on a surface perpendicular to the first main surface PS1 of the filter portion 10 is a rectangle. Specifically, the sectional shape of the through hole 11 is a rectangle whose side in the circumferential direction D1 of the filtration filter 1A has a length larger than that in the thickness direction of the filtration filter 1A. The sectional shape of the through hole 11 is not limited to a rectangle and may be, for example, a tapered shape such as a trapezoid or a parallelogram, a symmetrical shape, or an asymmetrical shape.

The non-continuous portion 14 is formed by shifting a part of the continuous portion 13 in the direction D2 orthogonal to the circumferential direction D1 of the filtration filter 1A. Specifically, the non-continuous portion 14 is formed by shifting, in the longitudinal direction (Y direction) of the filtration filter 1A, the parts of the continuous portion 13 extending in the lateral direction (X direction) of the filtration filter 1A.

The non-continuous portion 14 denotes the part where the parts of the filter base 12 extending in the circumferential direction D1 of the filtration filter 1A or the parts of the filter base 12 extending in the direction D2 orthogonal to the circumferential direction D1 have inflection points and where the parts branch off in three directions from the inflection points.

As illustrated in FIGS. 2 and 3, the filter base 12 includes a first filter base 12a, which extends, in the non-continuous portion 14, in the direction D2 (Y direction) orthogonal to the circumferential direction D1 (X direction) of the filtration filter 1A. In addition, the filter base 12 includes a plurality of second filter bases 12b and a plurality of third filter bases 12c. The second filter bases 12b are connected to a first side of the first filter base 12a in the circumferential direction D1 (X direction) of the filtration filter 1A. The third filter bases 12c are connected to a second side of the first filter base 12a opposite the first side in the circumferential direction D1 (X direction) of the filtration filter 1A. The second filter bases 12b and the third filter bases 12c are integrally formed.

A plurality of first connection portions 15 and a plurality of second connection portions 16 are formed in the non-continuous portion 14. The second filter bases 12b and the first filter base 12a are connected at the respective first connection portions 15. The third filter bases 12c and the first filter base 12a are connected at the respective second connection portions 16.

The first connection portions 15 and the second connection portions 16 are separated from each other in the first filter base 12a. Specifically, the first connection portions 15 are each disposed between two second connection portions 16 adjacent to each other. In other words, the first connection portions 15 are each disposed between corresponding adjacent second connection portions 16.

For this reason, in the non-continuous portion 14, a plurality of first through holes 11a and a plurality of second through holes 11b, which are adjacent to the first through holes 11a, are arranged so as to be shifted from each other in the direction D2 (Y direction) orthogonal to the circumferential direction D1 of the filtration filter 1A. The first through holes 11a and the second through holes 11b are arranged in the non-continuous portion 14 in the height direction (Y direction) of the filtration filter 1A, that is, in the direction D2 orthogonal to the circumferential direction D1 of the filtration filter 1A.

As described above, in the filtration filter 1A, the non-continuous portion 14 is formed by shifting a part of the continuous portion 13 in the direction D2 (Y direction) orthogonal to the circumferential direction D1 (X direction) of the filtration filter 1A. The number of the connection portions in the non-continuous portion 14 to which the filter base 12 is connected can be larger than that in the continuous portion 13. The connection portions in the continuous portion 13 are the parts where the parts of the filter base 12 extending in the lateral direction (X direction) of the filtration filter 1A and the parts of the filter base 12 extending in the longitudinal direction (Y direction) of the filtration filter 1A intersect and are connected to each other. The connection portions in the non-continuous portion 14 denote the first connection portions 15 and the second connection portions 16.

More connection portions are formed in the non-continuous portion 14 than in the continuous portion 13, and stress is thus more likely to be concentrated on the non-continuous portion 14 than on the continuous portion 13. For this reason, the non-continuous portion 14 is more likely than the continuous portion 13 to be broken or deformed when subjected to an external force. That is, the non-continuous portion 14 can be more easily cut than the continuous portion 13. In addition, the non-continuous portion 14 has sufficient strength not to be broken by a force generated by a fluid flowing during filtration. As described above, the filtration filter 1A can be easily cut when subjected to an external force while maintaining sufficient strength to withstand filtration. As a result, after filtration with the filtration filter 1A is finished, the filtration objects captured by the filtration filter 1A can be easily observed by applying an external force to the non-continuous portion 14 to cut the non-continuous portion 14.

In Embodiment 1, the width of the first filter base 12a, which forms the non-continuous portion 14, is equal to the width of a part forming the continuous portion 13 of the filter base 12. Specifically, in the non-continuous portion 14, the width of the first filter base 12a extending in the direction D2 (Y direction) orthogonal to the circumferential direction D1 (X direction) of the filtration filter 1A having a cylindrical shape is equal to the width of the part forming the continuous portion 13 of the filter base 12. The term "equal" allows a margin of error of 10%.

The frame portions 20 are parts disposed at the respective ends of the filter portion 10 having a cylindrical shape. The frame portions 20 are each shaped into a ring when viewed from one end or the other end of the filter portion 10 having a cylindrical shape.

Filter information (for example, the dimensions of the through hole 11) may be indicated on the frame portions 20. This enables a user to grasp the hole dimensions of the through hole 11 without, for example, further measurement.

In Embodiment 1, the material forming the frame portions 20 is the same as the material forming the filter portion 10 (filter base 12).

In Embodiment 1, the filtration filter 1A having a cylindrical shape has a diameter of 12 mm, a height of 22 mm, and a film thickness of 2 µm. Each side of the through hole 11 having a square shape has a length of 6 µm. The filter base 12 has a width of 2.5 µm. The dimensions of the filtration filter 1A are not limited thereto, and the filtration filter 1A may be produced with other dimensions.

[Operation]

Figure 4:
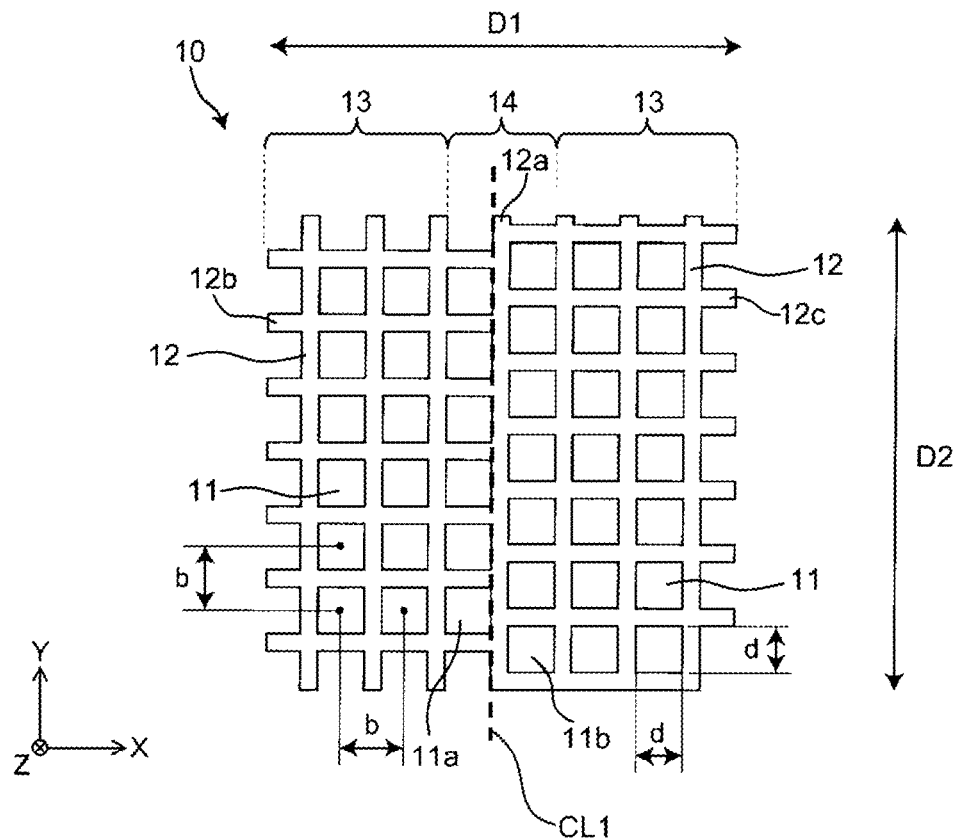
FIG. 4 illustrates an example of a method for cutting the filtration filter in Embodiment 1 according to the present invention.

A method for cutting the filtration filter 1A is described with reference to FIG. 4. FIG. 4 illustrates an example of a method for cutting the filtration filter 1A in Embodiment 1 according to the present invention.

As illustrated in FIG. 4, the filtration filter 1A having a cylindrical shape can be easily cut by cutting the non-continuous portion 14 along a cutting line CL1, which extends in the height direction (Y direction) of the filtration filter 1A.

Cutting is performed with, for example, tweezers and a knife.

[Manufacturing Method]

Next, an example of a method for manufacturing the filtration filter 1A is described with reference to FIGS. 5A to 5E. FIGS. 5A to 5E are schematic diagrams each illustrating an example of a step of a method for manufacturing the filtration filter 1A in Embodiment 1 according to the present invention. FIGS. 5A to 5E each illustrate a step performed before the filtration filter 1A is formed into a cylindrical shape.

Figure 5A:
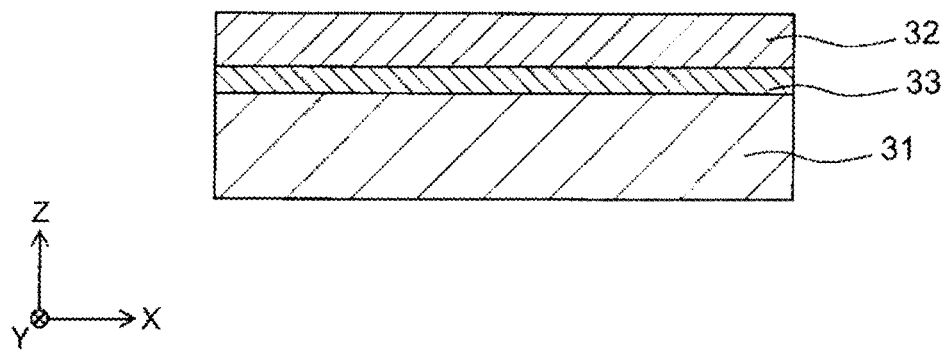
FIG. 5A is a schematic diagram illustrating an example of a step of a method for manufacturing the filtration filter in Embodiment 1 according to the present invention.
Figure 5:
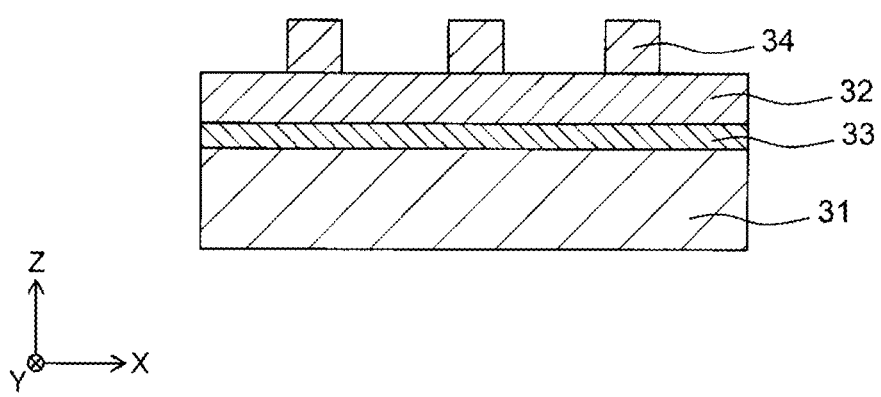
FIG. 5B is a schematic diagram illustrating an example of a step of the method for manufacturing the filtration filter in Embodiment 1 according to the present invention.
FIG. 5C is a schematic diagram illustrating an example of a step of the method for manufacturing the filtration filter in Embodiment 1 according to the present invention.
FIG. 5D is a schematic diagram illustrating an example of a step of the method for manufacturing the filtration filter in Embodiment 1 according to the present invention.
FIG. 5E is a schematic diagram illustrating an example of a step of the method for manufacturing the filtration filter in Embodiment 1 according to the present invention.
Figure 5:
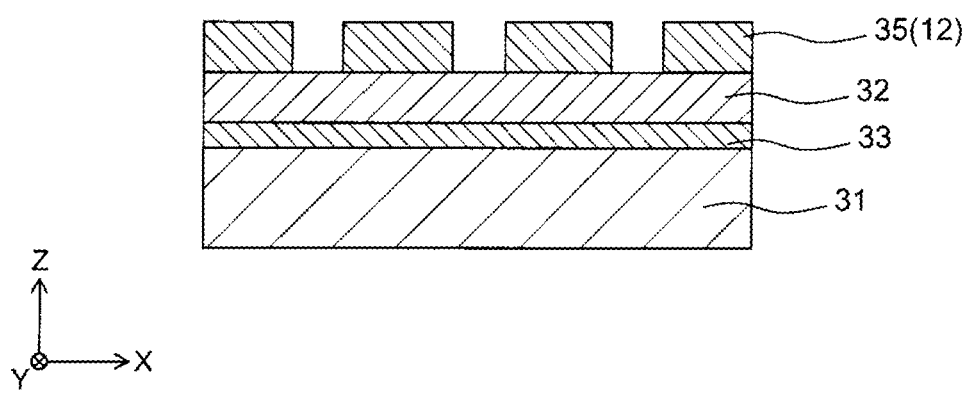

As illustrated in FIG. 5A, a copper thin film 32 having a thickness of 1.5 µm is formed above a substrate 31 made of, for example, silicon. The copper thin film 32 can be formed by vapor deposition or sputtering. In this case, an intermediate layer 33 made of titanium and having a thickness of 0.5 µm is formed to improve the adhesiveness between the substrate 31 and the copper thin film 32.

Next, a resist film having a thickness of 2 µm is formed by applying a resist onto the copper thin film 32 by spin coating and then by drying the resist.

As illustrated in FIG. 5B, a resist film 34 is exposed and developed, and the parts of the resist film 34 whose positions correspond to the position of the filter base 12 are removed. The hole shape is a square shape.

As illustrated in FIG. 5C, the filter base 12 made of a nickel coating film 35 is formed, by electroforming, at the positions where the resist film 34 is removed. Subsequently, the filtration filter 1A that is yet to be formed into a cylindrical shape is produced by removing the resist film 34 by using an organic solvent.

When the filtration filter 1A alone is formed into a cylindrical shape, the filtration filter 1A may deform due to a fluid. Thus, the mechanical strength of the filtration filter has to be improved. For this reason, a reinforcing layer 36 is formed on circumferential portions and on the center line portion of the filtration filter 1A. The reinforcing layer 36 has a thickness of 20 µm. The through holes 11 each having a square shape whose side has a length of 290 µm are arranged, in a square grid array at intervals of 10 µm, in the part of the reinforcing layer 36 disposed on the filter base 12.

Figure 5D:
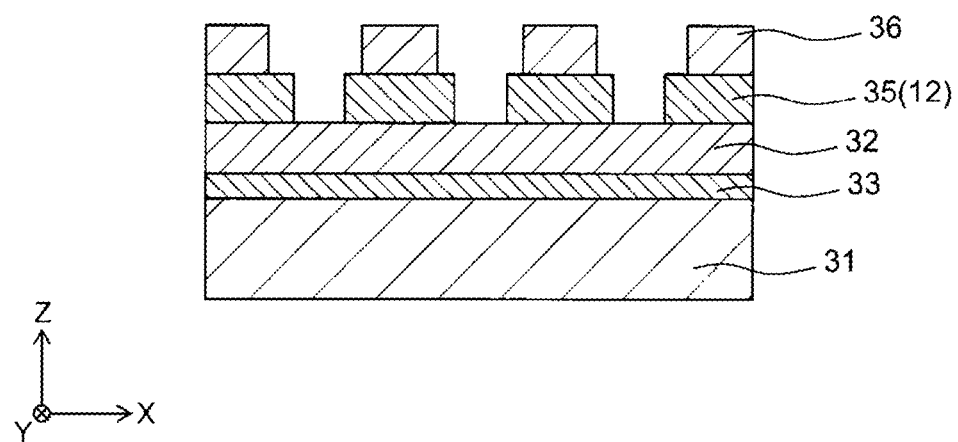
Figure 5E:
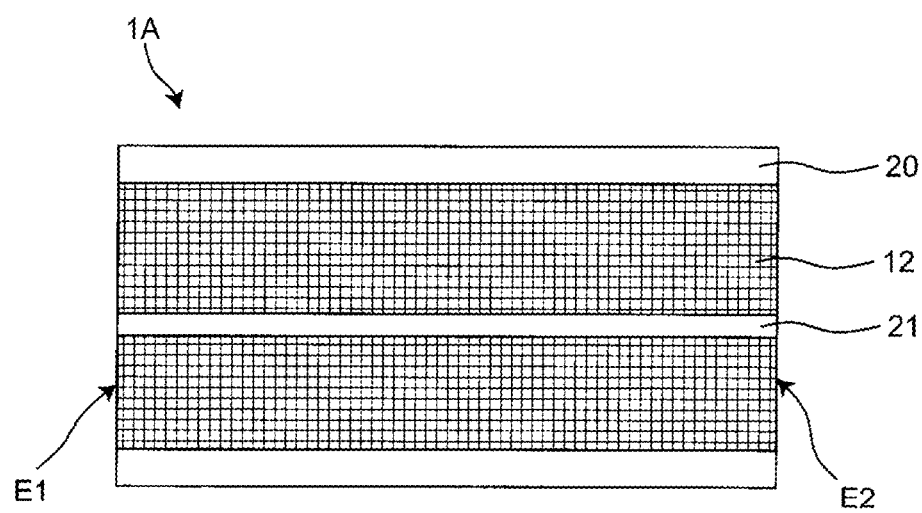

In the reinforcing layer 36, by a process similar to the process in FIGS. 5A to 5C, the resist film 34 having a thickness of 30 µm is formed and then exposed and developed to remove the parts of the resist film 34 at the positions of the circumferential portions and the center line portion of the filtration filter 1A. As illustrated in FIG. 5D, the reinforcing layer 36 made of a nickel coating film is formed, by electroforming, at the positions where the resist film 34 is removed. As illustrated in FIG. 5E, the filtration filter 1A having an open area percentage of 50% and having the through holes 11 each having a side having a length of 6 µm is produced by removing the resist film 34 by using an organic solvent. In this step, the filtration filter 1A is a rectangular film filter. The frame portions 20 and a support portion 21 of the filtration filter 1A are formed by the reinforcing layer 36.

In the method for manufacturing the filtration filter 1A in Embodiment 1, although an example in which the reinforcing layer 36 is formed on the filtration filter 1A is described, the reinforcing layer 36 is not an essential component.

Figure 6A:
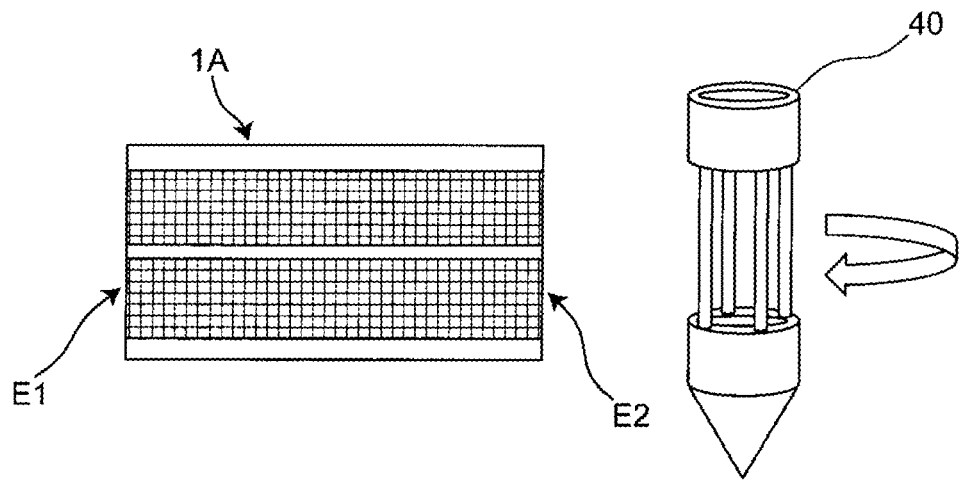
FIG. 6A is a schematic diagram illustrating an example of a method for forming the non-continuous portion.
Figure 6B:
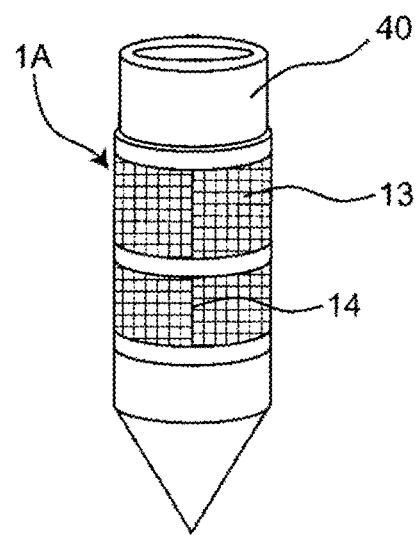
FIG. 6B is a schematic diagram illustrating an example of the method for forming the non-continuous portion.

Next, an example of a method for forming the filtration filter 1A into a cylindrical shape is described with reference to FIGS. 6A and 6B. FIGS. 6A and 6B are schematic diagrams each illustrating an example of a method for forming the non-continuous portion 14.

As illustrated in FIG. 6A, the filtration filter 1A is wound around a container 40, which has a cylindrical shape and is made of a polyacetal resin. The container 40 is a container having a bottom. The side wall of the container 40, around which the filtration filter 1A is wound, is open. The container 40 is an example of a container used for filtration and is not limited thereto.

Specifically, tape is attached to the circumferential portions of the filtration filter 1A, which is a film filtration filter having one end E1 and another end E2, and the filtration filter 1A is then wound around the container 40 to roll the filtration filter 1A into a cylindrical shape and fix the filtration filter 1A. More specifically, double-sided tape (TackLiner TL-450S-16 produced by LINTEC Corporation) having a thickness of 50 µm and whose base material is a polyester film to which a light coating of an acrylic adhesive is applied is attached to the circumferential portions of the filtration filter 1A such that the double-sided tape fits the widths of the circumferential portions in the X direction and the Y direction. A space of 3 mm in which the double-sided tape is not attached is formed in the lengthwise direction (X direction) in a part of the circumferential portions at the other end E2. The filtration filter 1A to which the double-sided tape is attached is wound around the container 40 to roll the filtration filter 1A into a cylindrical shape and fix the filtration filter 1A.

As illustrated in FIG. 6B, the one end E1 and the other end E2 of the filtration filter 1A are joined with epoxy resin by using an optical microscope and a micromanipulator. Specifically, the one end E1 and the other end E2 are joined by applying epoxy resin to the joint interface between the one end E1 and the other end E2 and to the space between the container 40 and the circumferential portions of the filtration filter 1A. In this case, the one end E1 and the other end E2 are joined so as to be shifted from each other such that the through holes 11 are not arranged continuously. As a result, the non-continuous portion 14 is formed in the joint region where the one end E1 and the other end E2 are joined. More specifically, the grids in the joint region are aligned by moving, using the micromanipulator, the part of the circumferential portions at the other end E2, to which the double-sided tape is not attached, through the optical microscope at a magnification of 1000 times. After the alignment, the one end E1 and the other end E2 are tentatively fixed with tape and joined by applying epoxy resin to the joint interface between the one end E1 and the other end E2 and to the space between the container 40 and the circumferential portions of the filtration filter 1A.

[Observation Method of Filtration Objects]

After finishing filtration of filtration objects by using the filtration filter 1A having a cylindrical shape, the non-continuous portion 14 of the filtration filter 1A is cut with tweezers and a knife. Specifically, the epoxy resin with which the one end E1 and the other end E2 of the filtration filter 1A are joined is cut and peeled, and the non-continuous portion 14 is gradually peeled from the container 40 with tweezers beginning with its circumference portion. As a result, the filtration filter 1A having a cylindrical shape is cut along the non-continuous portion 14, and thus it is possible to directly observe, by using a microscope, the filtration objects captured by the second main surface PS2 of the filtration filter 1A. In particular, when the filtration objects are cells, it is possible to observe the filtration objects without damaging the cells.

[Stress Analysis Simulation]

The following description provides the results of stress analysis simulations, with Femtet produced by Murata Manufacturing Co., Ltd., of the stress generated in the non-continuous portion 14 of the filter portion 10.

Figure 7:
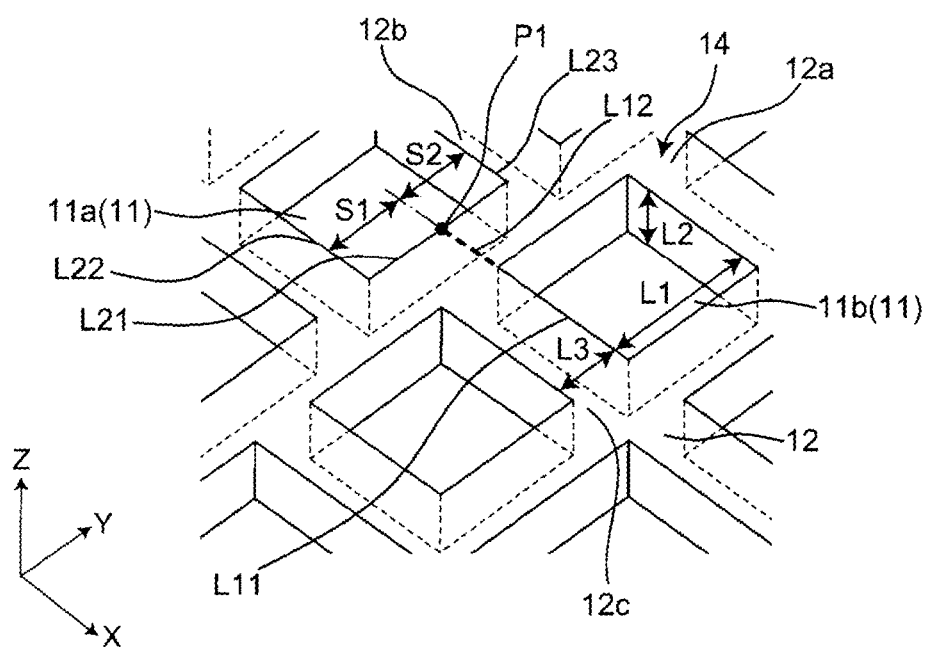
FIG. 7 is an enlarged schematic diagram illustrating an example of an analytical model used for a stress analysis simulation.

FIG. 7 is an enlarged schematic diagram illustrating an example of an analytical model used for a stress analysis simulation. As illustrated in FIG. 7, in a filtration filter used in the analytical model, through holes 11 each having a square shape are arranged in a square grid array. A side L1 of each through hole 11 of the filter in the analytical model has a length of 12 µm, and a depth L2 of the through hole 11 is 5 µm. A width L3 of a filter base 12 is 5 µm. The material forming the filter in the analytical model is nickel.

Shift lengths S1 and S2 between arrays of first through holes 11a and second through holes 11b formed in a non-continuous portion 14 vary in stress analysis simulations. The shift length S1 denotes the distance from a point P1 to a lower side L22 of a first through hole 11a. At the point P1, an extension line L12, which is formed by extending a lower side L11 of a second through hole 11b in the non-continuous portion 14 in the lateral direction (X direction) of the filter, and a side L21 of the first through hole 11a intersect each other. The shift length S2 denotes the distance from the point CP1, where the extension line L12 and the side L21 of the first through hole 11a intersect each other, to an upper side L23 of the first through hole 11a. The shift length S2 can be calculated by the equation: S2=(12−S1).

In the stress analysis simulations, the shift lengths S1 and S2 are adjusted, and stress analyses are performed on Comparative Example 1, in which there are no shifts, and Example 1, in which there are shifts. In Comparative Example 1, S1 is 0 µm, and S2 is 12 µm. In Example 1, S1 is 8.5 µm, and S2 is 3.5 µm.

In each of the stress analysis simulations of Comparative Example 1 and Example 1, a filtration filter in an analytical model is pulled in the circumferential direction D1 of the filtration filter, that is, both the +X direction and the −X direction, and a surface load of 0.05 N/m$^2$ is applied to a main surface (first main surface PS1) of a non-continuous portion 14.

Figure 8A:
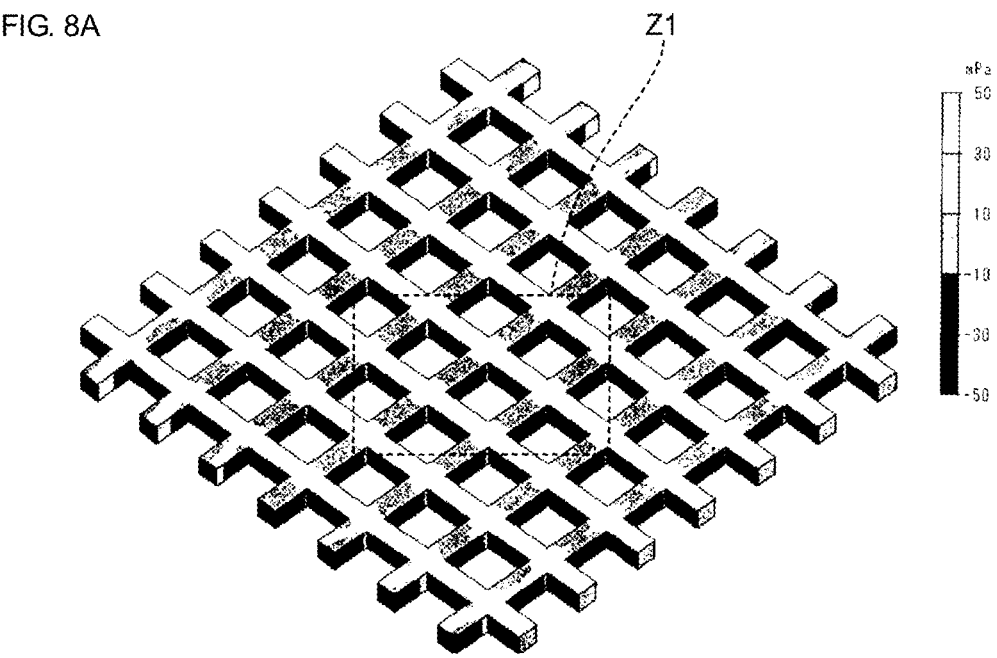
FIG. 8A illustrates an example of a result of a stress analysis simulation of an analytical model in Comparative Example 1.
Figure 8B:
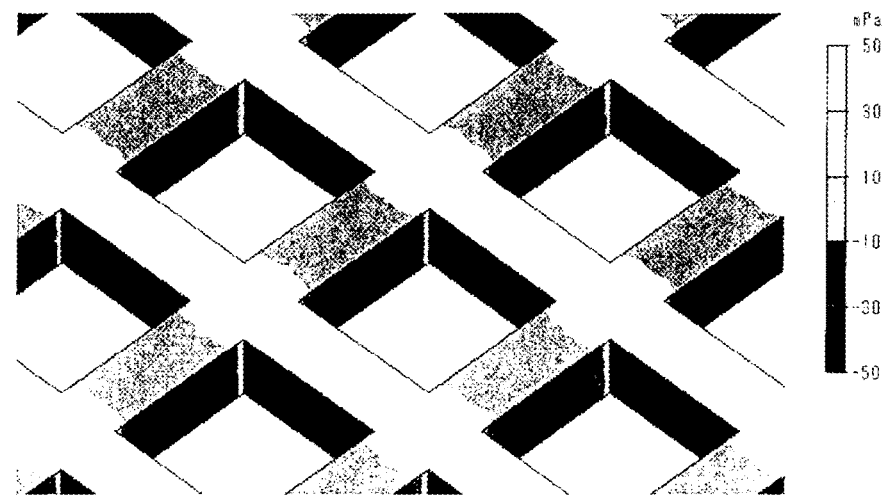
FIG. 8B is an enlarged view of section Z1 in Comparative Example 1 in FIG. 8A.
Figure 9A:
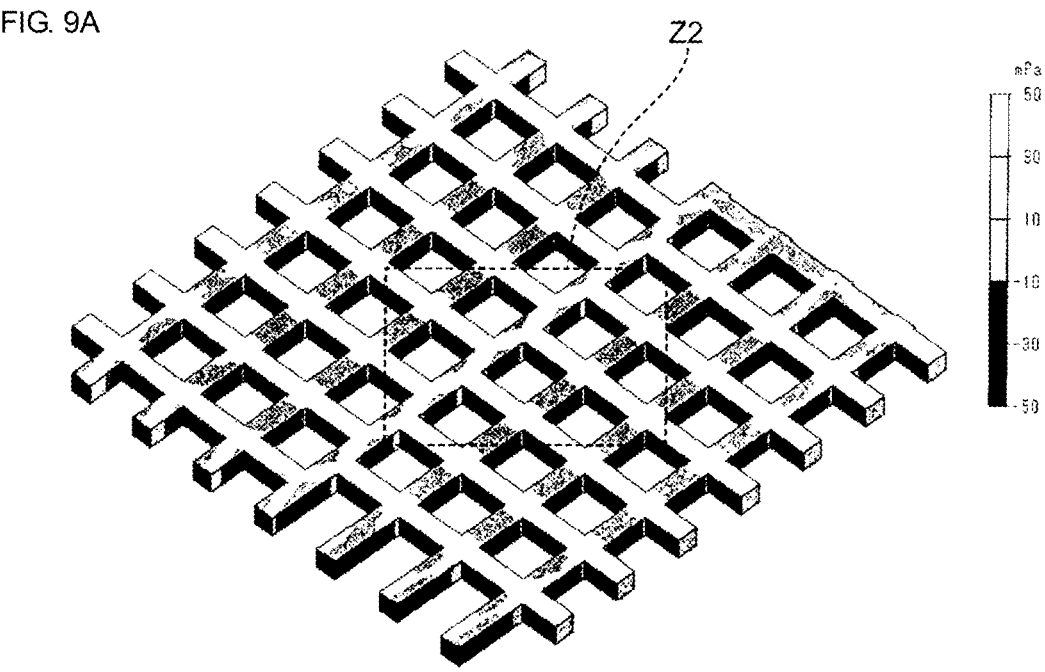
FIG. 9A illustrates an example of a result of a stress analysis simulation of an analytical model in Example 1.
Figure 9B:
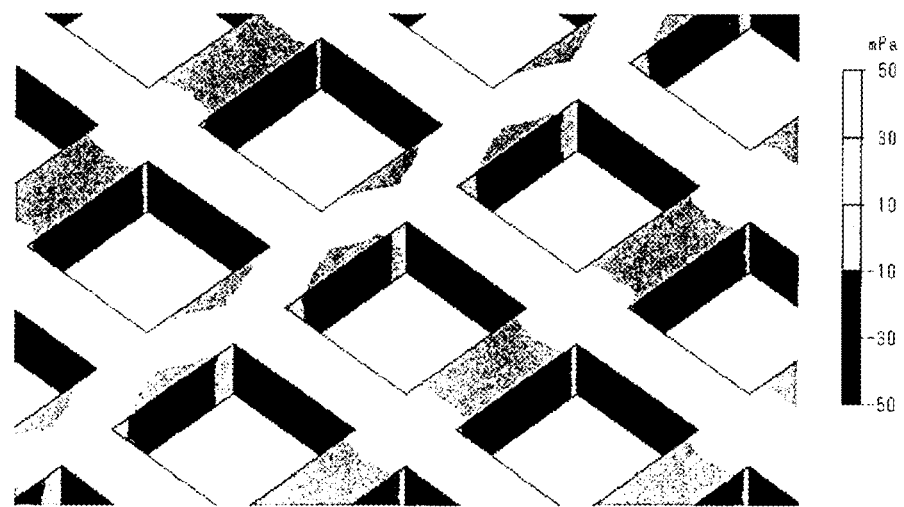
FIG. 9B is an enlarged view of section Z2 in Example 1 in FIG. 9A.

FIG. 8A illustrates an example of a result of the stress analysis simulation of the analytical model in Comparative Example 1. FIG. 8B is an enlarged view of section Z1 in Comparative Example 1 in FIG. 8A. FIG. 9A illustrates an example of a result of the stress analysis simulation of the analytical model in Example 1. FIG. 9B is an enlarged view of section Z2 in Example 1 in FIG. 9A. As illustrated in FIGS. 8A, 8B, 9A, and 9B, the area where stress is generated in the non-continuous portion 14 in Example 1 is wider than that in Comparative Example 1. This is because the number of connection portions of a filter base 12 in the non-continuous portion 14 in Example 1 is larger than that in Comparative Example 1. Stress is likely to be generated in the connection portions of the filter base 12, and thus it is considered that the number of parts where stress is generated in Example 1 is larger than that in Comparative Example 1.

Next, the stress applied to the non-continuous portion 14 in the longitudinal direction (Y direction) of the filter is analyzed by using the filter in the analytical model.

Figure 10:
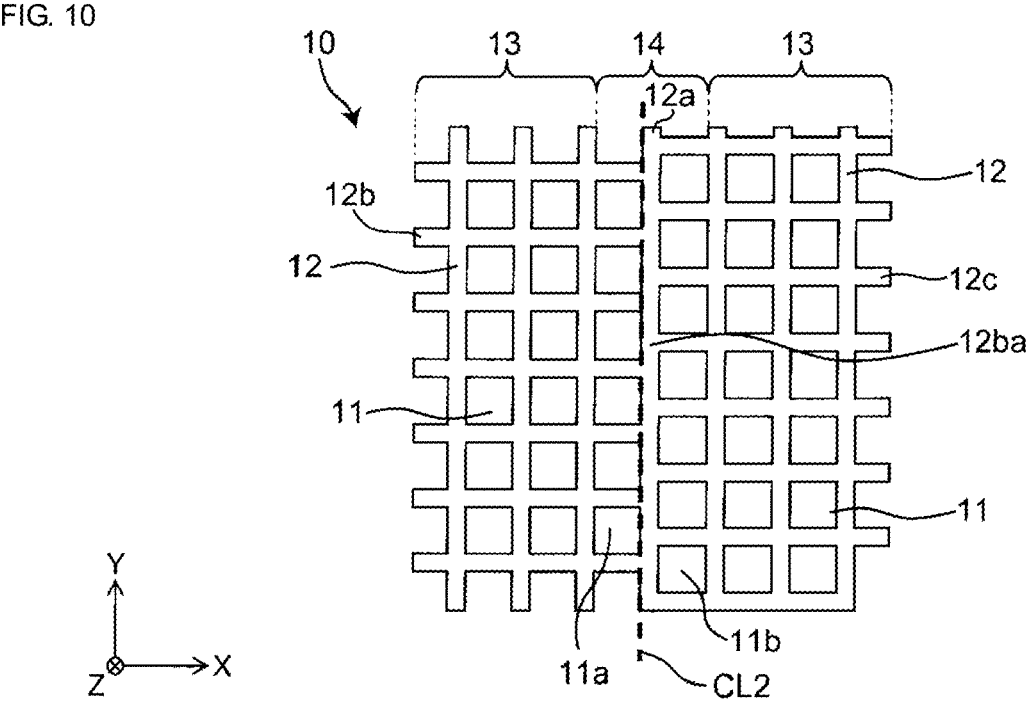
FIG. 10 illustrates a part of a non-continuous portion of a filter of the analytical model on which a stress analysis is performed.
Figure 11:
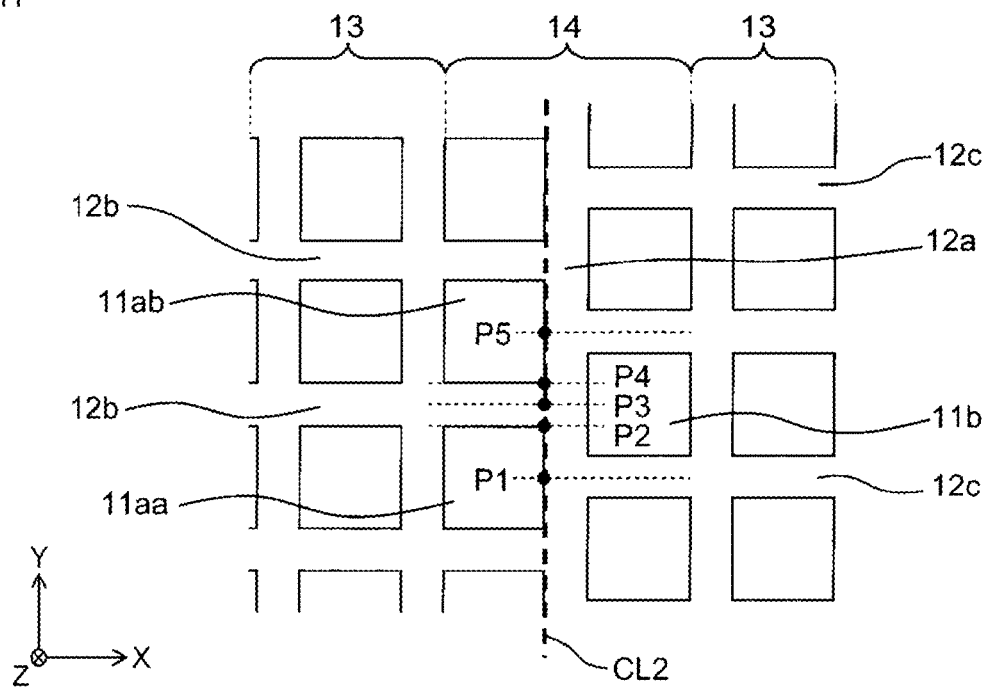
FIG. 11 illustrates a detailed position at which the stress analysis is performed.

FIG. 10 illustrates a part of the non-continuous portion 14 of the filter of the analytical model on which a stress analysis is performed. FIG. 11 illustrates a detailed position at which the stress analysis is performed. As illustrated in FIGS. 10 and 11, a stress analysis is performed on the non-continuous portion 14 along an analysis line CL2, which extends on the sides facing the second through holes 11b of the first through holes 11a. The through holes 11 are formed periodically in the filter in the analytical model, and thus it is considered that the stress distribution has periodicity. For this reason, the length between two through holes 11aa and 11ab, which are adjacent to each other in the longitudinal direction (Y direction) of the filter, is regarded as one period. In the stress analysis simulations, as illustrated in FIG. 11, five analysis positions P1 to P5 are set on the analysis line CL2 between the two through holes 11aa and 11ab, and the stress generated at each analysis position is analyzed. The through hole 11aa is disposed below the through hole 11ab.

As illustrated in FIG. 11, the analysis position P1 is positioned at the center of the side on the analysis line CL2 of the through hole 11aa. The analysis position P2 is positioned above the analysis position P1 and at a corner of the through hole 11aa. The analysis position P3 is positioned on the first filter base 12a between the through hole 11aa and the through hole 11ab, which is adjacent to the through hole 11aa, and is a position where the distance from the corner of the through hole 11aa to the analysis position P3 is equal to the distance from a corner of the through hole 11ab to the analysis position P3. The analysis position P4 is positioned above the analysis position P3. In addition, the analysis position P4 is positioned at the corner of the through hole 11ab, which is disposed closer to the through hole 11aa. The analysis position P5 is positioned at the center of the side on the analysis line CL2 of the through hole 11ab.

Comparative Example 2 and Example 2 to Example 9 are used in the stress analysis simulations whose parameters are shifts between the arrays of the first through holes 11a and the second through holes 11b. An analytical model in Comparative Example 2 has a shift of 0% and does not include the non-continuous portion 14. Analytical models in Example 2 to Example 9 respectively have a shift of 1%, 5%, 10%, 20%, 40%, 60%, 80%, and 100%.

Figure 12A:
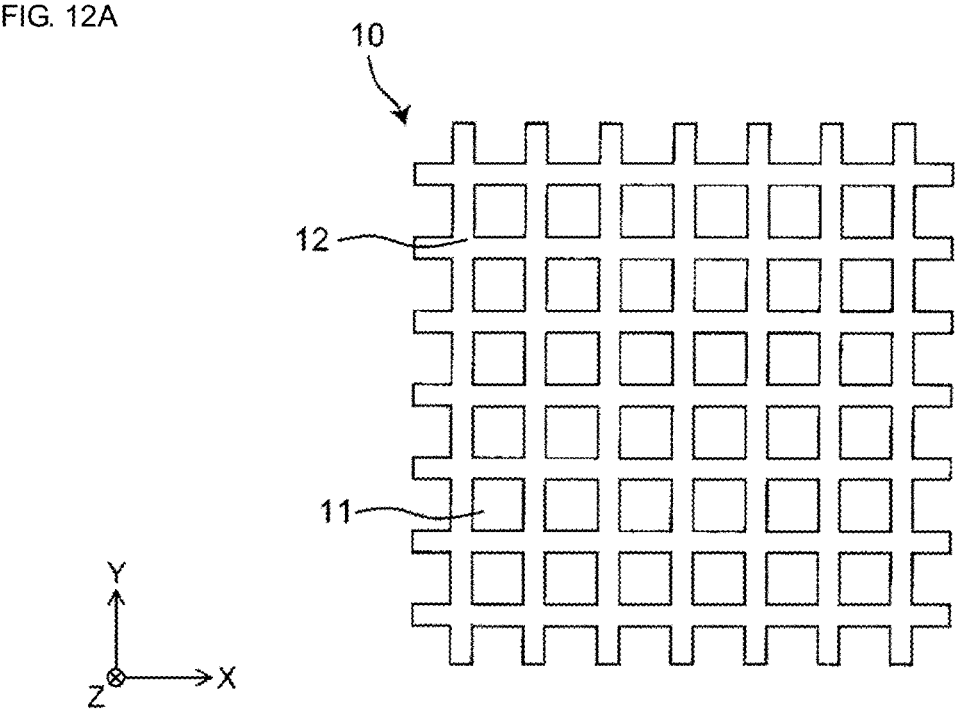
FIG. 12A illustrates a schematic configuration of an analytical model in Comparative Example 2.
Figure 12B:
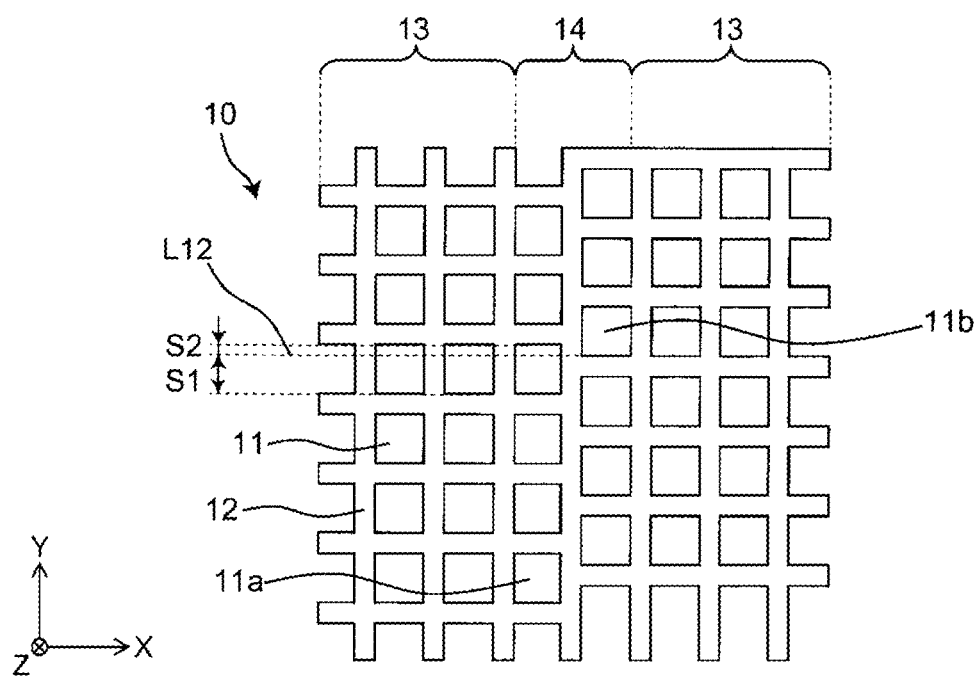
FIG. 12B illustrates a schematic configuration of an analytical model in Example 9.

FIG. 12A illustrates a schematic configuration of the analytical model in Comparative Example 2. FIG. 12B illustrates a schematic configuration of the analytical model in Example 9. As illustrated in FIG. 12A, the analytical model in Comparative Example 2 has a shift of 0% and does not include the non-continuous portion 14. The shift of 0% denotes that all the through holes 11 are arranged in a square grid array. In other words, in FIG. 7, Comparative Example 2 has a configuration in which S1 is 0 µm and S2 is 12 µm. As illustrated in FIG. 12B, the analytical model in Example 9 has a shift of 100%, that is, the largest shift between the first through holes 11a and the second through holes 11b in the non-continuous portion 14. In FIG. 7, the shift of 100% denotes a configuration in which S1 is 8.5 µm and S2 is 3.5 µm. S1 becomes larger as S2 becomes smaller in Example 2 to Example 8 in this order, and thus the shift ratio is changed.

Figure 13:
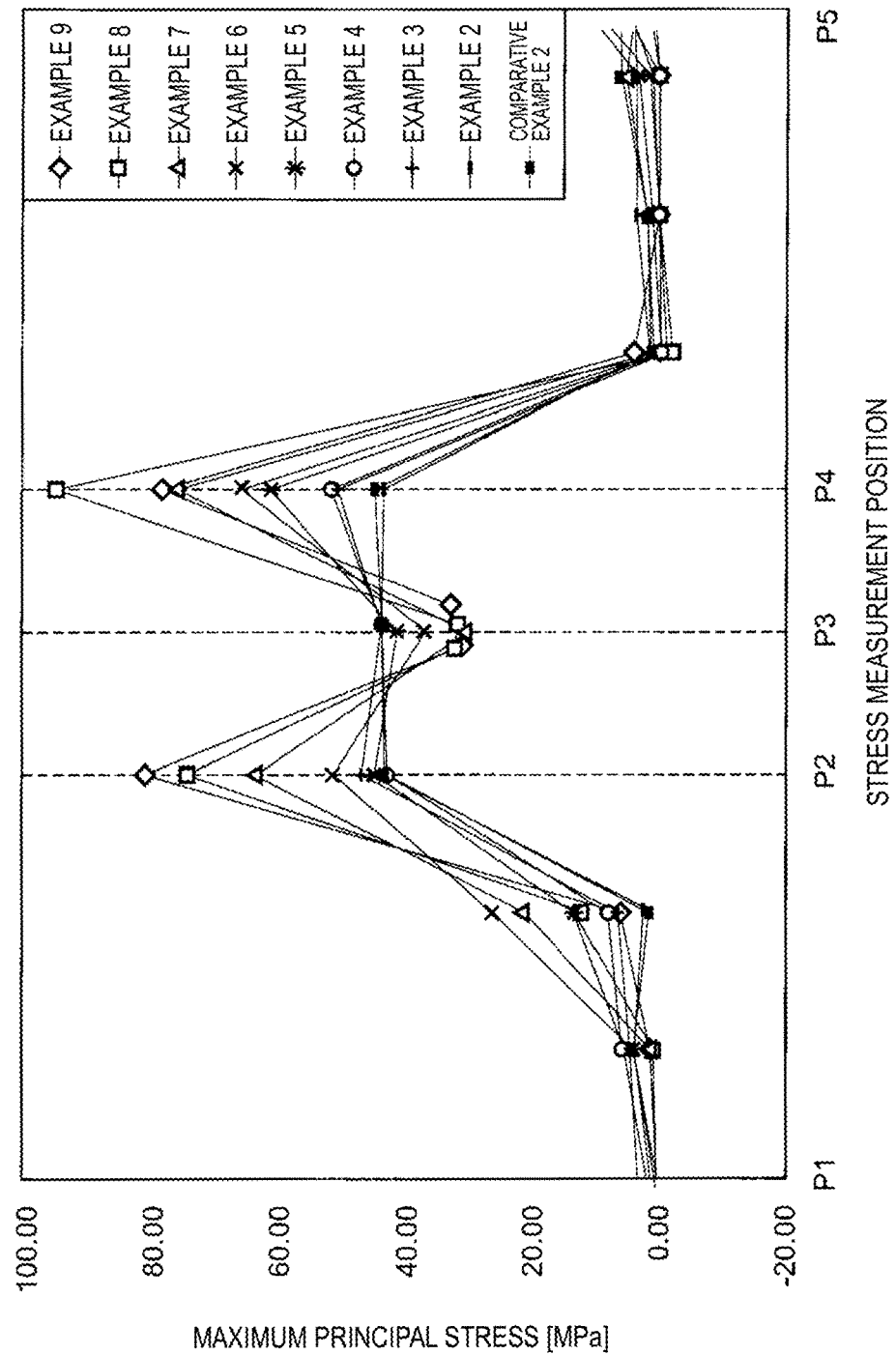
FIG. 13 illustrates an example of stress analysis results in Comparative Example 2 and Example 2 to Example 9.

FIG. 13 illustrates an example of stress analysis results in Comparative Example 2 and Example 2 to Example 9. As illustrated in FIG. 13, the maximum principal stresses in the vicinities of the analysis positions P2 and P4 in each of Example 3 to Example 9 are higher than those in Comparative Example 2. The number of the connection portions of the filter base 12 in the non-continuous portion 14 in each of Example 3 to Example 9 is larger than that in Comparative Example 2. Thus, stress is likely to be concentrated on the connection portions. For this reason, it is possible to easily break the non-continuous portion 14. In the vicinity of the analysis position P3, the maximum principal stress becomes lower as the shift ratio becomes higher. From this, it is considered that cracking or chipping is unlikely to occur in the vicinity of the analysis position P3.

As described above, when the shift between the first through holes 11a and the second through holes 11b is 5% or more, the stress generated in each connection portion of the filter base 12 in the non-continuous portion 14 is high compared with the case in which the shift is 0%. Thus, it is possible to easily break the non-continuous portion 14.

It is considered that a similar level of stress is generated, by applying a load, also in the connection portions of the filter base 12 on both sides of an analysis target connection portion. For this reason, it is considered that a crack in the connection portion of the filter base 12 is linked to cracks in the connection portions of the filter base 12 on both sides by applying a high load, and thus it is possible to more easily break the non-continuous portion 14.

Also in Example 2, the connection portions of the filter base 12 in the non-continuous portion 14 are shifted from each other at the end faces of the filter in the longitudinal direction. For this reason, when the non-continuous portion 14 is cut with tweezers and a knife after filtration, compared with Comparative Example 2, it is possible to cut the non-continuous portion 14 with the high probability of successful cutting or damage to the surface reduced because the non-continuous portion 14 in Example 2 has hold portions and spaces.

FIG. 14 illustrates the relationships between the maximum principal stresses in Example 2 to Example 9 relative to the maximum principal stress in Comparative Example 2. The maximum principal stresses at the analysis positions P4 in Comparative Example 2 and Example 2 to Example 9 are used in FIG. 14. As illustrated in FIG. 14, the maximum principal stresses in Example 3 to Example 9 become higher, relative to the maximum principal stress in Comparative Example 2, in the order of Example 3, Example 4, Example 5, Example 6, Example 7, Example 9, and Example 8. Although the shift in Example 8 is smaller than that in Example 9, the maximum principal stress in Example 8 is higher than that in Example 9.

As described above, the maximum principal stress at the analysis position P4 in the configuration in which the shift is 5 to 100% is higher than the maximum principal stress at the analysis position P4 in the configuration in which the shift is 0%, and the maximum principal stress in the configuration in which the shift is 80% is highest.

[Filtration]

Figure 15A:
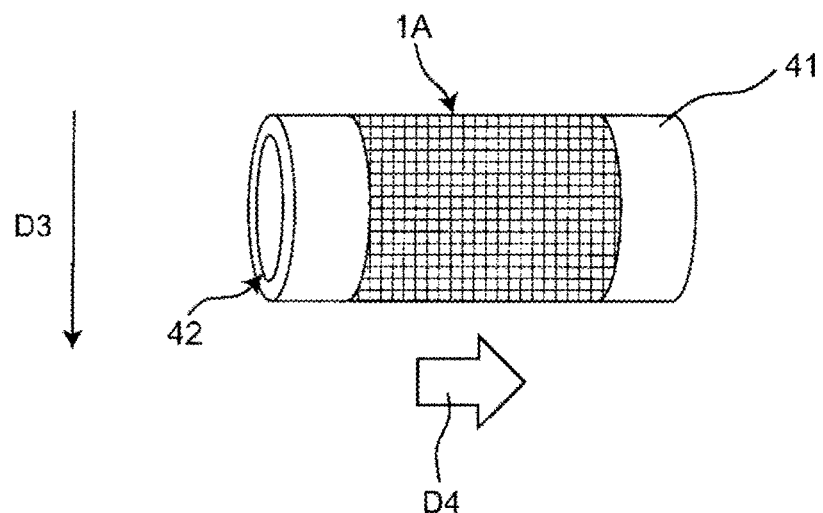
FIG. 15A illustrates an example of a state in which filtration is performed with the filtration filter in Embodiment 1 according to the present invention.

FIG. 15A illustrates an example of a state in which filtration is performed with the filtration filter 1A in Embodiment 1 according to the present invention. As illustrated in FIG. 15A, the filtration filter 1A is attached to a side wall of a container 41 having a cylindrical shape. The container 41 to which the filtration filter 1A is attached is disposed in a direction D4 orthogonal to the gravity direction D3. In other words, the container 41 is disposed such that an inlet 42, which is an inlet for a fluid containing filtration objects, faces in the direction D4 orthogonal to the gravity direction D3. As a result, a fluid flows inside the filtration filter 1A in the direction D4 and flows parallel to the second main surface PS2 of the filtration filter 1A. In this case, it is considered that the load due to gravity and the shear stress due to fluid friction are dominant as the stress applied to the non-continuous portion 14. In the example illustrated in FIG. 15A, gravity effect is large. Thus, the non-continuous portion 14 is preferably disposed at an upper position in the filtration filter 1A in the gravity direction D3. As a result, it is possible to avoid applying the load in the gravity direction D3 to the non-continuous portion 14 and thus to inhibit the non-continuous portion 14 from being broken during filtration.

Figure 15B:
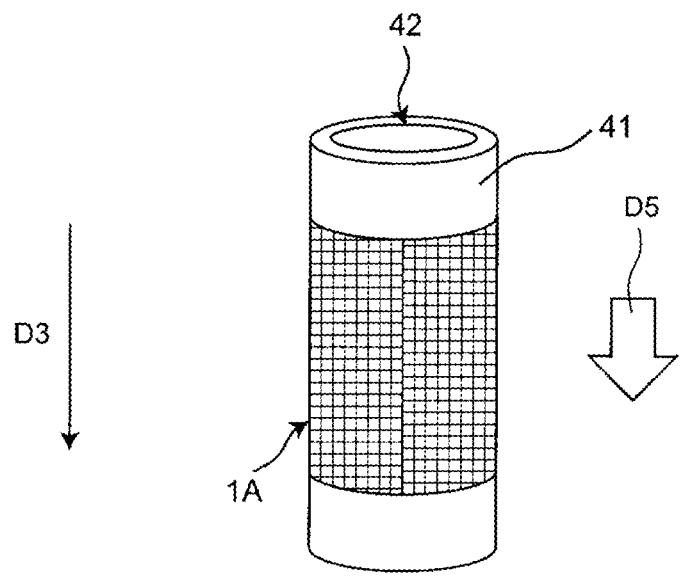
FIG. 15B illustrates another example of a state in which filtration is performed with the filtration filter in Embodiment 1 according to the present invention.

FIG. 15B illustrates another example of a state in which filtration is performed with the filtration filter 1A in Embodiment 1 according to the present invention. As illustrated in FIG. 15B, the cylindrical container 41 to which the filtration filter 1A is attached may be disposed in the gravity direction D3. In other words, the container 41 is disposed such that the inlet 42, which is an inlet for a fluid containing filtration objects, faces upward. As a result, a fluid flows in a direction D5, which is the same direction as the gravity direction D3, and flows parallel to the second main surface PS2 of the filtration filter 1A. As described above, the load in the gravity direction D3 is unlikely to be applied to the non-continuous portion 14. Thus, it is possible to inhibit the non-continuous portion 14 from being broken during filtration.

In both FIGS. 15A and 15B, wall surfaces of the connection portions of the filter base 12 in the non-continuous portion 14 are disposed in a direction in which a fluid flows. Thus, the effect of flow viscosity is dominant in the shear force applied to the non-continuous portion 14. The shear stress applied in the immediate vicinity of the wall surface is determined by a viscosity and a velocity gradient in accordance with the Newtonian law of viscosity. The velocity gradient is considered to be linear like a laminar flow only in the vicinity of the wall surface and thus is determined by a flow velocity and the circle diameter of the filtration filter 1A. The viscosity of a liquid such as water typically used as a fluid is as low as several mPa/s or less. When water at 20° C. flows, at $5 \times 10^{-1}$ m/s, inside the filtration filter 1A having a cylindrical shape and a radius of 6 mm, the shear stress applied to the wall surface of the filtration filter 1A is about 42 mPa. The strength of epoxy resin is several hundred MPa. Thus, provided that even if a light coating of epoxy resin is applied, the epoxy resin is sufficiently cured, it is considered that the possibility that the non-continuous portion 14 is broken during filtration is extremely low.

The filtration filter 1A may be used in an inclined state relative to the gravity direction D3.

At the time of observation, as illustrated in FIG. 4, the filtration filter 1A can be cut by being subjected to an external force in a direction in which the non-continuous portion 14 is cut and peeled to cut the non-continuous portion 14 along the cutting line CL1.

[Effects]

The filtration filter 1A according to Embodiment 1 can provide the following effects.

The filtration filter 1A is a filter having a tubular shape. The filtration filter 1A includes the filter base 12, which defines the plurality of through holes 11 arranged in a square grid array. The filter base 12 includes the continuous portion 13 and the non-continuous portion 14. The continuous portion 13 is formed continuously in the direction D2 from the first opening 2 of the filtration filter 1A toward the second opening 3 of the filtration filter 1A, and in the circumferential direction D1 along the circumference of a section of the filtration filter 1A in the direction orthogonal to the direction D2 from the first opening 2 of the filtration filter 1A toward the second opening 3 of the filtration filter 1A. The non-continuous portion 14 is formed by shifting a part of the continuous portion 13 in the direction D2 from the first opening 2 of the filtration filter 1A toward the second opening 3 of the filtration filter 1A. Such a configuration enables the filtration filter 1A to be easily cut by being subjected to an external force after finishing filtration without being broken by a fluid force during cross-flow filtration. As a result, it is possible to easily observe the filtration objects captured inside the filtration filter 1A.

As described above, the filtration filter 1A having a tubular shape can be easily cut by being subjected to an external force while maintaining sufficient strength to withstand filtration.

The filter base 12 includes the first filter base 12a, which extends, in the non-continuous portion 14, in the direction D2 orthogonal to the circumferential direction D1 of the filtration filter 1A. In addition, the filter base 12 includes the plurality of second filter bases 12b and the plurality of third filter bases 12c. The second filter bases 12b are connected to the one side of the first filter base 12a in the circumferential direction D1 of the filtration filter 1A. The third filter bases 12c are connected to the other side of the first filter base 12a in the circumferential direction D1 of the filtration filter 1A. The plurality of first connection portions 15 and the plurality of second connection portions 16 are shifted from each other in the direction D2 orthogonal to the circumferential direction D1 of the filtration filter 1A. The second filter bases 12b and the first filter base 12a are connected at the respective first connection portions 15. The third filter bases 12c and the first filter base 12a are connected at the respective second connection portions 16.

With such a configuration, the first connection portions 15 and the second connection portions 16, which are separated from each other, are formed in the first filter base 12a, which forms the non-continuous portion 14. This enables the number of the connection portions in the non-continuous portion 14 to be larger than that in the continuous portion 13, and thus stress is likely to be generated in the connection portions in the non-continuous portion 14. As a result, the filtration filter 1A having a cylindrical shape can be more easily cut by being subjected to an external force while maintaining sufficient strength to withstand filtration.

The first connection portions 15 are each disposed between corresponding adjacent second connection portions 16. Such a configuration enables the filtration filter 1A to be more easily cut by being subjected to an external force.

The width of the first filter base 12a, which forms the non-continuous portion 14, is equal to the width of the part forming the continuous portion 13 of the filter base 12. With such a configuration, stress is likely to be generated in the non-continuous portion 14 by applying an external force to the non-continuous portion 14. Thus, the filtration filter 1A having a cylindrical shape can be more easily cut.

The filtration filter 1A is a film filter having the one end E1 and the other end E2 and is formed into a cylindrical shape by joining the one end E1 to the other end E2. The non-continuous portion 14 is formed in the joint region where the one end E1 and the other end E2 are joined. Such a configuration enables the non-continuous portion 14 to be easily formed and the filtration filter 1A to be more easily cut by being subjected to an external force.

The filter base 12 contains at least one of a metal and a metal oxide as a main component. With such a configuration, the non-continuous portion 14 is unlikely to be broken by a force generated by a fluid flowing during filtration but is likely to be cut by being subjected to an external force. That is, the filtration filter 1A can be easily cut by being subjected to an external force while having improved mechanical strength.

The distance between the first through hole 11a and the second through hole 11b that are positioned adjacent to each other across the interface between the non-continuous portion 14 and the continuous portion 13 (interface where the non-continuous portion 14 and the continuous portion 13 are shifted from each other) can be larger than the distance between two through holes 11 that are adjacent to each other at a position outside the interface. The through holes 11 and a filter base 12 are arranged regularly to increase the open area percentage. Since the distance between the first through hole 11a and the second through hole 11b that are adjacent to each other so as to be shifted from each other in the interface can be large, it is possible to narrow the first filter base 12a in the interface and thus to equalize the distance between the through holes 11 that are adjacent to each other in the interface with the distance between the through holes 11 that are adjacent to each other in a region outside the interface. Such a configuration enables the open area percentage to be increased and thus filtration efficiency to be improved.

Embodiment 1 is advantageous in the case in which filtration objects are cells and a fluid is a cell suspension.

Although an example in which the filtration filter 1A is formed into a cylindrical shape by joining the one end E1 to the other end E2 is described in Embodiment 1, the present invention is not limited thereto. For example, the filtration filter 1A may be integrally formed. In other words, the continuous portion 13 and the non-continuous portion 14 may be integrally formed. For example, in the step illustrated in FIG. 5B, a pattern of the filtration filter 1A in which a pattern of the continuous portion 13 and a pattern of the non-continuous portion 14 are integrally formed can be integrally formed by performing exposure and development with a mask in which the pattern of the continuous portion 13 and the pattern of the non-continuous portion 14 are joined.

Although an example in which the one end E1 and the other end E2 of the filtration filter 1A are joined with epoxy resin is described in Embodiment 1, the present invention is not limited thereto. For example, the one end E1 and the other end E2 may be joined by welding.

Although an example in which the non-continuous portion 14 is formed in the direction D2 (Y direction) orthogonal to the circumferential direction D1 (X direction) of the filtration filter 1A is described in Embodiment 1, the present invention is not limited thereto. It is simply required that the non-continuous portion 14 be formed in a direction intersecting the circumferential direction D1 of the filtration filter 1A. For example, the non-continuous portion 14 may be formed so as to be inclined relative to the circumferential direction D1 of the filtration filter 1A. In addition, one or more non-continuous portions 14 may be formed. For example, when the filtration filter 1A needs to be divided for analyzing filtration objects within a field of view of a microscope, recultivating filtration objects in a six-well plate, or other reasons, the filtration filter 1A can be cut into desired-sized filtration filters after processing by forming the non-continuous portion 14 at a plurality of parts of the filtration filter 1A. In such a manner, one or more non-continuous portions 14 may be formed. As described above, the non-continuous portion 14 may be formed at a plurality of parts of the filtration filter 1A.

Although an example in which filtration objects are observed by cutting the filtration filter 1A having a cylindrical shape and by setting the cut filtration filter on an optical microscope is described in Embodiment 1, the present invention is not limited thereto. For example, filtration objects may be collected by cutting the filtration filter 1A having a cylindrical shape.

Although an example in which the filtration filter 1A has a cylindrical shape is described in Embodiment 1, the present invention is not limited thereto. For example, the filtration filter 1A may have a section in the direction orthogonal to the direction D2 having a circular tubular shape, an oval tubular shape, or a polygonal tubular shape.

Embodiment 2

A filtration filter in Embodiment 2 according to the present invention is described.

The differences between Embodiment 2 and Embodiment 1 are described mainly in Embodiment 2. In the description in Embodiment 2, the components identical or similar to those in Embodiment 1 have the same reference signs. Overlapping descriptions between Embodiment 2 and Embodiment 1 are omitted.

Embodiment 2 differs from Embodiment 1 in that a non-continuous portion includes a flat portion.

Figure 16:
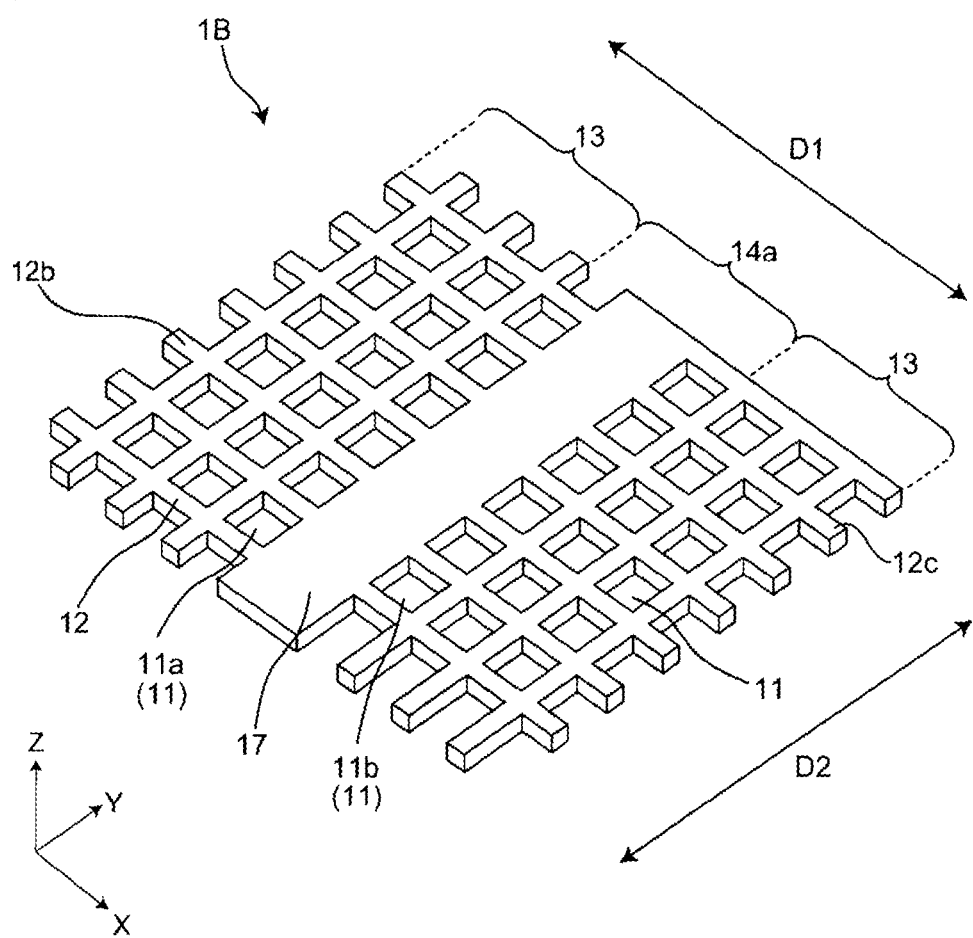
FIG. 16 is a schematic perspective view of an example of a part of a filtration filter in Embodiment 2 according to the present invention.

FIG. 16 is a schematic configuration diagram of an example of a part of a filtration filter 1B in Embodiment 2 according to the present invention. As illustrated in FIG. 16, in the filtration filter 1B, a non-continuous portion 14a includes a flat portion 17, which extends in a direction D2 orthogonal to a circumferential direction D1 of the filtration filter 1B.

Specifically, the flat portion 17 is a part formed by widening the width of the first filter base 12a in Embodiment 1. That is, the flat portion 17 is a part of a filter base 12. The flat portion 17 is formed between a plurality of first through holes 11a and a plurality of second through holes 11b, which are formed in the non-continuous portion 14a. The width direction of the flat portion 17 denotes the lateral direction (X direction) of the filtration filter 1B. The thickness of the flat portion 17 is equal to the thickness of the filter base 12. The flat portion 17 is made of the same material as the material forming the filter base 12.

In Embodiment 2, the flat portion 17 has a width of 25 µm.

In the filtration filter 1B, the first through holes 11a and the second through holes 11b are arranged so as to be shifted from each other with the flat portion 17 interposed therebetween. That is, a plurality of second filter bases 12b are connected to one side of the flat portion 17 in the circumferential direction D1 of the filtration filter 1B. A plurality of third filter bases 12c are connected to the other side of the flat portion 17 in the circumferential direction D1 of the filtration filter 1B.

[Stress Analysis Simulation]

The following description provides the results of analysis simulations, with Femtet produced by Murata Manufacturing Co., Ltd., of the stress generated in the non-continuous portion 14a.

In the stress analysis simulations, stress analyses are performed with analytical models having a configuration similar to that of the filtration filter 1B. The conditions of the stress analyses are similar to those in Embodiment 1. Specifically, the shift lengths S1 and S2 between the first through holes 11a and the second through holes 11b in the non-continuous portion 14a are adjusted, and stress analyses are performed on Comparative Example 3, in which there are no shifts, and Example 10 to Example 14, in which there are shifts. In Comparative Example 3, an analytical model includes the flat portion 17, the shift between the first through holes 11a and the second through holes 11b is 0%, and all the through holes 11 are arranged in a square grid array. Analytical models of the filtration filter 1B in Example 10 to Example 14 respectively have a shift between the first through holes 11a and the second through holes 11b of 20%, 40%, 60%, 80%, and 100%.

Figure 17:
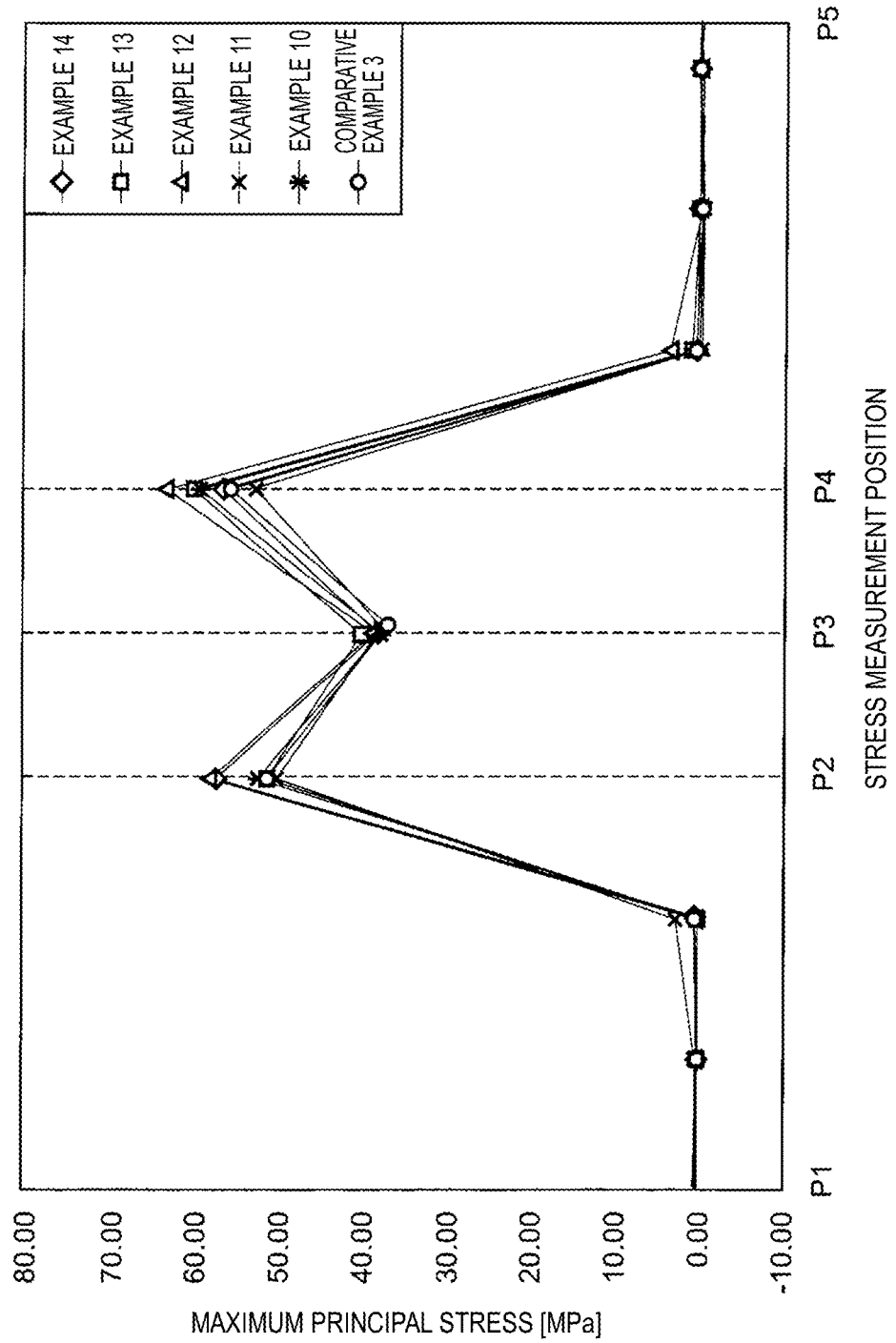
FIG. 17 illustrates an example of stress analysis results in Comparative Example 3 and Example 10 to Example 14.

FIG. 17 illustrates an example of stress analysis results in Comparative Example 3 and Example 10 to Example 14. As illustrated in FIG. 17, when focusing on the analysis positions P2 and P4, the maximum principal stresses in each of Example 12 to Example 14 are higher than the maximum principal stresses in Comparative Example 3. In other words, the maximum principal stress in the configuration in which the shift between the first through holes 11a and the second through holes 11b in the non-continuous portion 14a is 60% or more and 100% or less is higher than that in the configuration in which the shift is 0%. When comparing Comparative Example 3 with Example 14, the difference between the maximum principal stresses at each of the analysis positions P2 and P4 becomes smaller.

Next, to compare a configuration including the flat portion 17 with a configuration not including the flat portion 17, stress analysis simulations are performed with Comparative Example 4, Comparative Example 5, Example 15, and Example 16. A filter in Comparative Example 4 does not include the flat portion 17 and has a shift between the first through holes 11a and the second through holes 11b of 0%. A filter in Comparative Example 5 includes the flat portion 17 and has a shift of 0%. A filtration filter 1A in Example 15 does not include the flat portion 17 and has a shift of 100%. A filtration filter 1B in Example 16 includes the flat portion 17 and has a shift of 100%.

Figure 18:
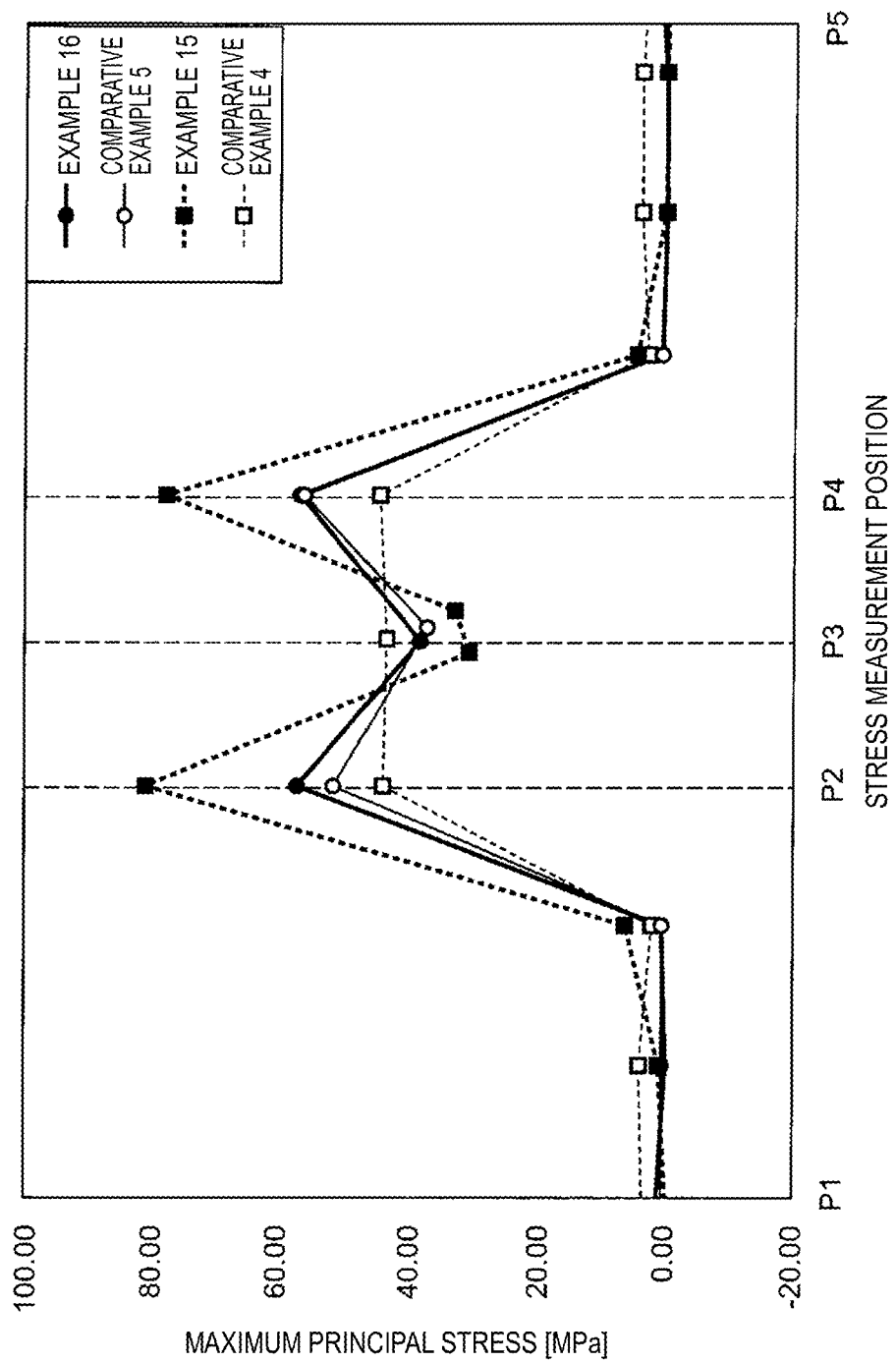
FIG. 18 illustrates an example of stress analysis results in Comparative Example 4 and Comparative Example 5, and Example 15 and Example 16.

FIG. 18 illustrates an example of stress analysis results in Comparative Example 4, Comparative Example 5, Example 15, and Example 16. When focusing on the maximum principal stresses at the analysis positions P2 and P4, the maximum principal stresses become higher in the order of Comparative Example 4, Comparative Example 5, Example 16, and Example 15.

[Effects]

The filtration filter 1B according to Embodiment 2 can provide the following effects.

In the filtration filter 1B, the non-continuous portion 14a includes the flat portion 17, which extends in the direction D2 orthogonal to the circumferential direction D1 of the filtration filter 1B having a cylindrical shape. The width of the flat portion 17 is larger than the width of the filter base 12. Such a configuration enables the strength of the non-continuous portion 14a to be higher than that of the non-continuous portion 14 in Embodiment 1. Thus, the strength against a fluid force during filtration is increased. On the other hand, the non-continuous portion 14a can be easily cut by being subjected to an external force. As a result, in the filtration filter 1B, the non-continuous portion 14a can be easily cut by being subjected to an external force while having improved mechanical strength. That is, the filtration filter 1B can also be easily cut by being subjected to an external force while maintaining sufficient strength to withstand filtration.

The width of the flat portion 17 is larger than the width of the filter base 12, and thus a regular array, that is, a square grid array, of the through holes 11 is interrupted in the non-continuous portion 14a. For this reason, stress is likely to be concentrated on the joint portions between the flat portion 17 and the filter bases 12b and 12c, which extend in the circumferential direction D1 of the filtration filter 1B. Thus, the non-continuous portion 14a of the filtration filter 1B can be easily cut by being subjected to an external force.

In addition, a thin blade, such as a knife, can be inserted into a space between the flat portion 17 and a container 40, and thus the adhesion surfaces between the flat portion 17 and the container 40 can be easily peeled from each other. As a result, the bonding degree of the non-continuous portion 14a can be reduced. Thus, the non-continuous portion 14a of the filtration filter 1B can be easily cut by being subjected to an external force.

The preferred embodiments of the present invention are sufficiently described with reference to the accompanying drawings. It is clear that various modifications and alterations can be made by those skilled in the art. It should be understood that such modifications and alterations are included within the scope of the present invention without departing from the scope of the present invention described in the accompanying claims.

The filtration filter of the present invention enables collected objects to be easily observed. Thus, the filtration filter is useful for fields of, for example, medicinal efficacy researches or production of regenerative medicines that uses cells.

REFERENCE SIGNS LIST 1A, 1B filtration filter
2 first opening
3 second opening
10 filter portion
11 through hole
12 filter base
12a first filter base
12b second filter base
12c third filter base
13 continuous portion
14 non-continuous portion
15 first connection portion
16 second connection portion
17 flat portion
20 frame portion
21 support portion
31 substrate
32 copper thin film
33 intermediate layer
34 resist film
35 coating film
36 reinforcing layer
40 container
41 container
42 inlet

The invention claimed is:

1. A filtration filter having a tubular shape and defining a first opening and a second opening facing the first opening, the filtration filter comprising:
   a filter base that defines a plurality of through holes arranged in a square grid array, wherein
   the filter base includes a continuous portion having a first set of through holes of the plurality of through holes and a non-continuous portion having a second set of through holes of the plurality of through holes, the continuous portion extending in a first direction from the first opening of the filtration filter toward the second opening of the filtration filter and extending in a second direction along at least a first portion of a circumference of the filtration filter orthogonal to the first direction, the non-continuous portion having a first row of the second set of through holes shifted with respect to a second row of the second set of through holes, the non-continuous portion extending in the first direction.

2. The filtration filter according to claim 1, further comprising:
   a first frame portion at the first opening of the filtration filter; and
   a second frame portion at the second opening of the filtration filter.

3. The filtration filter according to claim 1, wherein the non-continuous portion extends in the second direction along at least a second portion of the circumference of the filtration filter.

4. The filtration filter according to claim 1, wherein the filter base includes:
   a first filter base extending in the first direction in the non-continuous portion, the first filter base having a first side and a second side opposite the first side;
   a plurality of second filter bases connected to the first side of the first filter base at respective first connection portions, the plurality of second filter bases extending in the second direction; and
   a plurality of third filter bases connected to the second side of the first filter base at respective second connection portions, the plurality of third filter bases extending in the second direction, wherein
   the respective plurality of first connection portions and the respective plurality of second connection portions are shifted relative to each other in the first direction.

5. The filtration filter according to claim 4, wherein the respective first connection portions are each disposed between a corresponding adjacent two of the respective second connection portions.

6. The filtration filter according to claim 4, wherein a first width of the first filter base is equal to a second width of at least one of the plurality of second filter bases or at least one of the plurality of third filter bases.

7. The filtration filter according to claim 1, wherein
   the filtration filter is a film filter having a first end joined to a second end to form the tubular shape, and
   the non-continuous portion is in a joint region where the first end and the second end are joined.

8. The filtration filter according to claim 1, wherein the filter base comprises at least one of a metal and a metal oxide as a main component thereof.

9. The filtration filter according to claim 1, wherein a thickness of the filter base is one-tenth to ten times a size of a through hole of the plurality of through holes.

10. The filtration filter according to claim 1, wherein a main surface of the filter base configured to contact a fluid containing filtration objects has a surface roughness less than a size of the filtration objects.

11. A filtration filter comprising:
a filter base having a tubular shape with a first open end and a second open end facing the first open end, the filter base including:
a continuous portion having a first plurality of through holes arranged in a square grid array, the continuous portion extending in a first direction from the first open end toward the second open end and extending in a second direction along at least a first portion of a circumference of the filter base orthogonal to the first direction, and
a non-continuous portion having a second plurality of through holes that are offset relative to each other, the non-continuous portion extending in the first direction.

12. The filtration filter according to claim 11, further comprising:
a first frame portion at the first open end; and
a second frame portion at the second open end.

13. The filtration filter according to claim 11, wherein the non-continuous portion extends in the second direction along at least a second portion of the circumference of the filter base.

14. The filtration filter according to claim 11, wherein the filter base includes:
a first filter base extending in the first direction in the non-continuous portion, the first filter base having a first side and a second side opposite the first side;
a plurality of second filter bases connected to the first side of the first filter base at respective first connection portions, the plurality of second filter bases extending in the second direction; and
a plurality of third filter bases connected to the second side of the first filter base at respective second connection portions, the plurality of third filter bases extending in the second direction, wherein
the respective plurality of first connection portions and the respective plurality of second connection portions are shifted relative to each other in the first direction.

15. The filtration filter according to claim 14, wherein the respective first connection portions are each disposed between a corresponding adjacent two of the respective second connection portions.

16. The filtration filter according to claim 14, wherein a first width of the first filter base is equal to a second width of at least one of the plurality of second filter bases or at least one of the plurality of third filter bases.

17. The filtration filter according to claim 11, wherein
the filter base is a film filter having a first edge joined to a second edge to form the tubular shape, and
the non-continuous portion is in a joint region where the first end and the second end are joined.

18. The filtration filter according to claim 11, wherein the filter base comprises at least one of a metal and a metal oxide as a main component thereof.

19. The filtration filter according to claim 11, wherein a thickness of the filter base is one-tenth to ten times a size of a through hole of at least one of the first and second plurality of through holes.

20. The filtration filter according to claim 11, wherein a main surface of the filter base configured to contact a fluid containing filtration objects has a surface roughness less than a size of the filtration objects.

\* \* \* \* \*